United States Patent
Bernabei

(10) Patent No.: US 7,376,460 B2
(45) Date of Patent: May 20, 2008

(54) METHOD AND APPARATUS FOR SKIN ABSORPTION ENHANCEMENT AND TRANSDERMAL DRUG DELIVERY

(75) Inventor: Gian Franco Bernabei, Florence (IT)

(73) Assignee: Mattioli Engineering Ltd., London (GB)

( * ) Notice: Subject to any disclaimer, the term of this patent is extended or adjusted under 35 U.S.C. 154(b) by 11 days.

(21) Appl. No.: 11/494,567

(22) Filed: Jul. 28, 2006

(65) Prior Publication Data

US 2006/0264806 A1 Nov. 23, 2006

Related U.S. Application Data

(60) Division of application No. 10/784,913, filed on Feb. 24, 2004, now Pat. No. 7,083,580, which is a continuation-in-part of application No. 10/448,468, filed on May 30, 2003, now Pat. No. 6,980,854, which is a continuation-in-part of application No. 10/397,533, filed on Mar. 27, 2003, now Pat. No. 7,010,343, which is a continuation-in-part of application No. 10/201,644, filed on Jul. 24, 2002, now Pat. No. 6,748,266, which is a continuation-in-part of application No. 10/074,234, filed on Feb. 14, 2002, now Pat. No. 6,743,215, which is a continuation-in-part of application No. 09/942,044, filed on Aug. 30, 2001, now Pat. No. 6,687,537, which is a continuation-in-part of application No. 09/922,927, filed on Aug. 7, 2001, now Pat. No. 6,535,761.

(60) Provisional application No. 60/281,808, filed on Apr. 6, 2001.

(51) Int. Cl.
*A61N 1/30* (2006.01)
*A61H 1/00* (2006.01)

(52) U.S. Cl. .............................. 604/20; 601/15; 601/17
(58) Field of Classification Search .................. 604/20, 604/113–114; 601/15, 17; 607/3, 80
See application file for complete search history.

(56) References Cited

U.S. PATENT DOCUMENTS

| 4,141,359 A | 2/1979 | Jacobsen et al. | |
|---|---|---|---|
| 4,301,794 A | 11/1981 | Tapper | |
| 4,822,470 A | 4/1989 | Chang | |
| 4,887,594 A | 12/1989 | Siegel | |
| 4,907,601 A | 3/1990 | Frick | |
| 4,931,041 A | 6/1990 | Faeser | |
| 5,135,478 A | 8/1992 | Sibalis | |
| 5,320,597 A * | 6/1994 | Sage et al. | 604/20 |
| 5,320,598 A * | 6/1994 | Haak et al. | 604/20 |
| 5,445,611 A | 8/1995 | Eppstein et al. | |
| 5,538,503 A | 7/1996 | Henley | |

(Continued)

FOREIGN PATENT DOCUMENTS

EP 0 569 634 A 11/1993

(Continued)

*Primary Examiner*—Mark Bockelman
(74) *Attorney, Agent, or Firm*—Foley & Larnder LLP.

(57) ABSTRACT

A treatment method and apparatus for providing a substance to be absorbed onto a surface of a patient's skin, includes applying the substance onto the surface of the patient's skin by way of a probe head that provides, at the same time: i) bursts of electrical pulses to the skin surface, and ii) vibrations to the skin surface. The vibrations are applied to the skin surface at substantially a same frequency rate, a first harmonic of the same frequency rate, and/or a second harmonic of the same frequency rate, as a burst rate of electrical pulses being applied to the skin surface.

5 Claims, 20 Drawing Sheets

U.S. PATENT DOCUMENTS

| | | | |
|---|---|---|---|
| 5,624,415 | A | 4/1997 | Cormier et al. |
| 5,658,247 | A | 8/1997 | Henley |
| 5,667,487 | A | 9/1997 | Henley |
| 5,688,233 | A | 11/1997 | Hofmann et al. |
| 5,778,894 | A | 7/1998 | Dorogi et al. |
| 5,830,177 | A | 11/1998 | Li et al. |
| 5,879,322 | A * | 3/1999 | Lattin et al. ............ 604/20 |
| 5,983,131 | A | 11/1999 | Weaver et al. |
| 6,007,502 | A | 12/1999 | Lee |
| 6,009,345 | A | 12/1999 | Hofmann |
| 6,039,745 | A | 3/2000 | Di Fiore et al. |
| 6,041,253 | A | 3/2000 | Kost et al. |
| 6,302,874 | B1 | 10/2001 | Zhang et al. |
| 6,322,568 | B1 | 11/2001 | Bernabei et al. |
| 6,334,074 | B1 | 12/2001 | Spertell |
| 6,379,324 | B1 | 4/2002 | Gartstein et al. |
| 6,398,753 | B2 | 6/2002 | McDaniel |
| 6,424,862 | B1 | 7/2002 | Brown, III et al. |
| 6,443,914 | B1 | 9/2002 | Costantino |
| 6,517,499 | B1 | 2/2003 | Pereira |
| 6,527,783 | B1 | 3/2003 | Ignon |
| 6,535,761 | B2 | 3/2003 | Bernabei |
| 6,553,253 | B1 | 4/2003 | Chang |
| 6,687,537 | B2 | 2/2004 | Bernabei |
| 6,743,215 | B2 | 6/2004 | Bernabei |
| 6,748,266 | B2 | 6/2004 | Bernabei |
| 6,775,569 | B2 | 8/2004 | Mori et al. |
| 6,947,791 | B2 | 9/2005 | Zhang et al. |
| 2003/0014081 | A1 | 1/2003 | Bernabei |
| 2003/0088205 | A1 | 5/2003 | Chandrasekaran et al. |
| 2003/0138464 | A1 | 7/2003 | Zhang et al. |
| 2003/0187478 | A1 | 10/2003 | Bernabei |
| 2004/0015190 | A1 | 1/2004 | Bernabei |
| 2004/0167458 | A1 | 8/2004 | Draghia-Akli et al. |
| 2004/0220456 | A1 | 11/2004 | Eppstein |
| 2004/0220622 | A1 | 11/2004 | Bernabei |

FOREIGN PATENT DOCUMENTS

| | | |
|---|---|---|
| EP | 0 625 360 | 11/1994 |
| EP | 01286939 | 3/1996 |
| GB | 1077143 | 7/1967 |
| GB | 1444985 | 8/1973 |
| WO | WO 99/44678 | 9/1999 |
| WO | WO 00/02620 A1 | 1/2000 |
| WO | WO 02/49717 | 6/2002 |

* cited by examiner

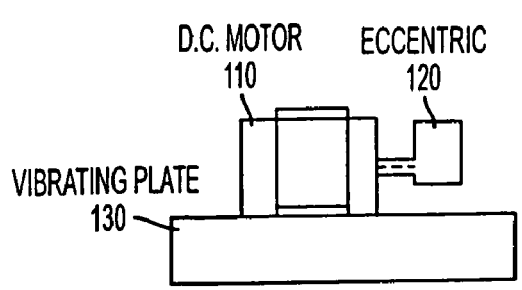
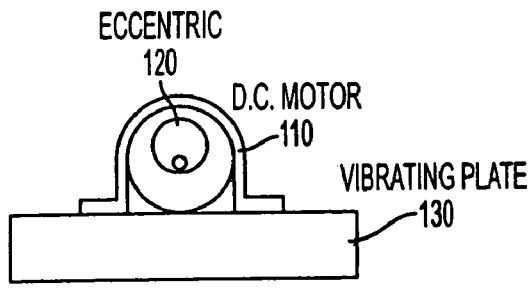
FIG. 1A    FIG. 1B
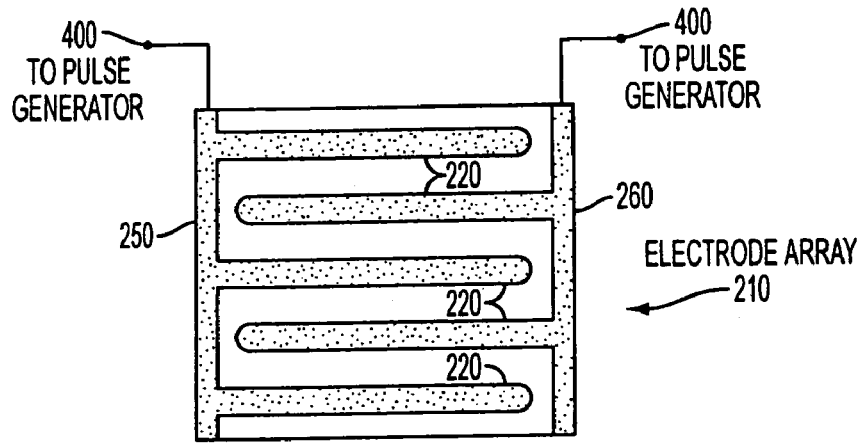
FIG. 2A
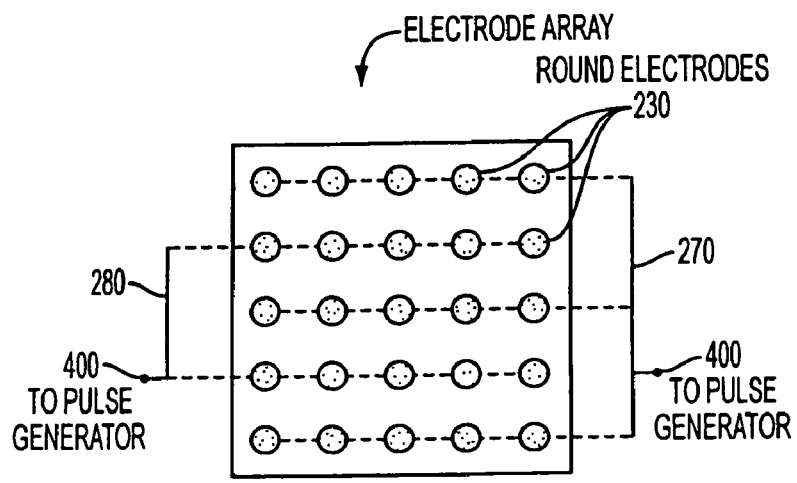
FIG. 2B

US 7,376,460 B2

METHOD AND APPARATUS FOR SKIN ABSORPTION ENHANCEMENT AND TRANSDERMAL DRUG DELIVERY

CROSS-REFERENCE TO RELATED PATENT APPLICATIONS

This application is a divisional of U.S. Ser. No. 10/784,913, filed Feb. 24, 2004, now U.S. Pat. No. 7,083,580 which is a continuation-in-part of U.S. Ser. No. 10/448,468, filed May 30, 2003, now U.S. Pat. No. 6,980,854, issued Dec. 27, 2005, which is a continuation-in-part of U.S. Ser. No. 10/397,533, filed Mar. 27, 2003, now U.S. Pat. No. 7,010,343, issued Mar. 7, 2006, which is a continuation-in-part of U.S. Ser. No. 10/201,644, filed Jul. 24, 2002, now U.S. Pat. No. 6,748,266, issued Jun. 8, 2004, which is a continuation-in-part of U.S. Ser. No. 10/074,234, filed Feb. 14, 2002, now U.S. Pat. No. 6,743,215, filed Jun. 1, 2004, which is a continuation-in-part of U.S. Ser. No. 09/942,044, filed Aug. 30, 2001, now U.S. Pat. No. 6,687,537, issued Feb. 3, 2004, which is a continuation-in-part of U.S. Ser. No. 09/922,927, filed Aug. 7, 2001, now U.S. Pat. No. 6,535,761, issued Mar. 18, 2003, which claims priority benefit to U.S. provisional 60/281,808, filed Apr. 6, 2001, each of which are incorporated by reference in their entirety.

BACKGROUND OF THE INVENTION

A. Field of the Invention

The invention relates to application of electrical pulses and mechanical vibrations to the skin in a controlled manner, in order to increase the absorption of a substance that is applied at the same time to the skin, whereby the substance is an ascorbic acid, lidocaine, collagen, or other type of skin treatment substance.

B. Description of the Related Art

It is known that an electrical pulse applied to the skin is useful in order to increase the absorption of a substance previously applied to the skin, whereby this technique is known as electroporation. Such a substance to be applied to the skin may be a liquid, a gel, a lotion, or a cream, for example.

It is desired to provide an apparatus and a method to increase the absorption of a substance to be applied to the skin, in order to obtain an increased (e.g., moisturizing) affect of the substance applied to the skin, as well as to obtain a fairly even absorption of the substance to the skin.

SUMMARY OF THE INVENTION

The present invention is directed to an apparatus and a method for enhancing the absorption of a substance to be applied on the skin.

To accomplish this, the present invention uses a sequence of electrical pulses (between 5 and 200 V peak to peak, preferably, and between 50 and 15,000 Hz preferably) provided to electrodes that are placed in contact with the skin. There is also provided a corresponding surface vibration to the skin, by application of a mechanical vibration to the skin. The mechanical vibration is provided by way of a vibrating plate that also contains the electrodes (which provide the electrical stimulus to the skin at the same time the mechanical vibration is provided to the skin).

The substance to be absorbed by the skin may applied to the skin by way of a probe or by a syringe. The syringe outputs the substance by way of a tube that is connected to an output of the syringe at one end of the tube and where the other end of the tube is disposed adjacent to a groove (or trough) surrounding a central electrode of an array of electrodes. Such a substance that is provided to the skin may be a cream, liquid or gel (for example, collagen, or cocoa butter, or suntan oil, or other types of skin enhancement lotions), or a drug to be administered into the skin.

The method according to an embodiment of the invention includes:

1) An apparatus which includes the following elements to perform the following treatment:

a) a probe having an array of electrodes on a head portion of the probe, with a central electrode disposed at a central location on the head portion and with a plurality of circumferential electrodes disposed around the central electrode.

b) a pulse generator connected to the array of electrodes.

c) a vibrator which vibrates the head portion of the probe at a same time the electrical pulses are provided to the array of electrodes on the head portion.

d) a syringe that provides a substance to the skin under control of a motor that outputs the substance from the syringe in a controlled manner, whereby the substance is provided to a groove or trough that surrounds the central electrode.

During operation, electrical pulses are provided to the skin by way of the electrodes on the head of the probe, and, at the same time, mechanical vibrations are provided to the skin by way of the vibrating head portion, whereby a substance to be applied to the skin is disposed within the trough surrounding the central electrode. The substance is absorbed within the skin due to the skin pores opening up as a result of the electrical pulses and mechanical vibrations being applied to the skin at the same time. Alternatively, only electrical pulses are provided to the skin, which does not provide as good a skin absorption effect as using both electrical pulses and mechanical vibrations. Also, gauze pads of hydrogel pads may be provided on a top surface of a plate on which the electrodes are disposed (instead of using a syringe), whereby the gauze pads are soaked with particular solutions to be applied to the patient's skin.

BRIEF DESCRIPTION OF THE DRAWINGS

The foregoing advantages and features of the invention will become apparent upon reference to the following detailed description and the accompanying drawings, of which:

FIG. 1A is a side view of a vibration mechanism that is disposed within an apparatus according to the present invention;

FIG. 1B is a front view of the vibration mechanism of FIG. 1A;

FIG. 2A shows an array of electrodes provided on an outer surface of the vibration plate that faces the skin, according to a first embodiment of the invention;

FIG. 2B shows an array of electrodes provided on an outer surface of the vibration plate that faces the skin, according to a second embodiment of the invention;

DETAILED DESCRIPTION OF THE PREFERRED EMBODIMENTS

Figure 2C:
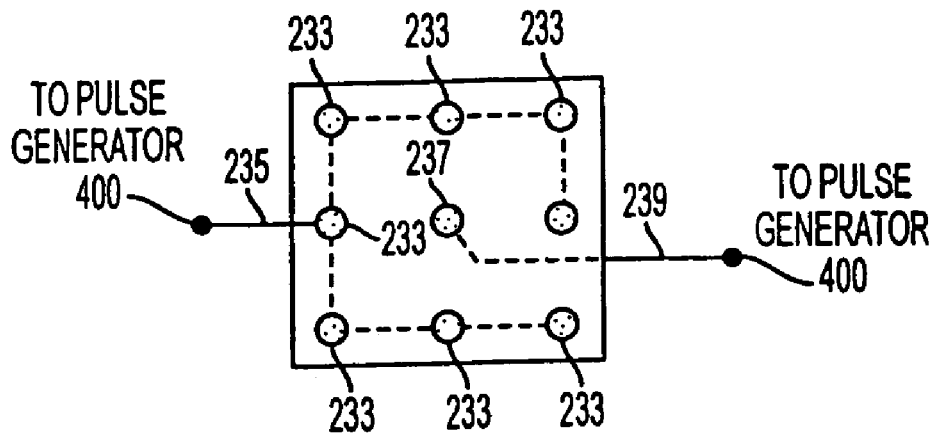
FIG. 2C shows an array of electrodes provided on an outer surface of the vibration plate that faces the skin, according to a third embodiment of the invention.

Preferred embodiments of the invention will be described in detail below, with reference to the accompanying drawings.

Based on experimental tests on the skin, it has been found by the inventor that after one or more pulses are applied between two points on the skin, transpiration (or absorption) in the area between the two points on the skin increases. The pulses that give optimal results are exponential pulses that are generated by a charged capacitor that is discharged on at least two separate points on the skin.

These experimental results have been utilized by the inventor in order to develop an apparatus and method that maintains the transpiration of the skin at a high level, so that the skin can readily absorb a gel, liquid, lotion, cream, or drug that is applied to the skin. The drug may be used to treat skin melanoma and/or cancerous tumors located just below the skin surface, for example.

The apparatus according to an embodiment of the present invention applies a sequence of pulses over an area or skin, by using an array of electrodes that are placed in contact with the skin. The array of electrodes are provided on a vibrating plate at the head of a probe, such as a hand-held probe 500 as shown in FIG. 5. The array of electrodes may be a configured as shown in FIG. 2A in a first embodiment, whereby odd rows of electrodes are electrically connected to each other, and thereby to a first output of a pulse generator 400 (see also FIG. 4) via a first electrical connection. The even rows of electrodes are electrically connected to each other, and also to a second output of the pulse generator 400 via a second electrical connection. The array of electrodes on the vibrating plate may alternatively be configured as shown in FIG. 2B in a second embodiment, whereby odd rows of round electrodes are electrically connected to each other, and thereby to the first output of the pulse generator 400 via a first electrical connection. The even rows of round electrodes are electrically connected to each other, and thereby to the second output of the pulse generator 400 via a second electrical connection.

The increase of the transpiration of the skin that is obtained by way of the present invention has the effect of increasing the absorption of liquids, creams, lotions, gels, or skin treatment drugs (or other kinds of drugs) that have been previously provided on the skin in the area between where the electrodes are applied to the skin.

The electrical pulses that are applied on the skin in order to enhance the transpiration of the skin are pulses obtained by a discharge of a capacitor on the skin. That is, the skin acts as a capacitive load when a probe is applied to the skin. A square-wave pulse input to a primary winding of the transformer 410 of FIG. 4, with an output of the secondary winding of the transformer 410 being coupled to the skin by way of the electrodes, provides the same effect as a discharging capacitor. However, by using a transformer 410 instead of a capacitor, one can obtain current control with respect to electrical pulses applied to the skin, so that the amount of current applied to the skin during treatment of the skin does not exceed a predetermined maximum current value.

The exponential pulses are generated during the rising edge and falling edge of each square-wave input pulse that is input to the transformer 410 from a square-wave pulse generator, and have opposite sign (positive exponential pulse due to the rising edge of a square-wave input pulse, negative exponential pulse due to the falling edge of the same square-wave input pulse). With the use of such a pulse generator 400 as shown in FIG. 4, it is possible to apply a burst of separate pulses (e.g., 500 to 1500 per second) to the skin, with adjacent pulses being of opposite polarity and which provides a transpiration effect better than just providing one pulse or many pulses of the same polarity to the skin.

Also, by outputting bursts of pulses to the skin in which each burst of pulses includes adjacent pulses in the same burst of opposite polarity (e.g., +−+−+−+−. . .), any potential current buildup in the skin is obviated due to the cancellation effect cause by utilizing adjacent pulses of opposite polarity. This is in contrast to the conventional devices that output electrical pulses of the same polarity, which may result in current buildup in a patient's skin, which may lead to damaging effects caused to the skin as a result of the current buildup.

As explained above, a burst pulse generator utilizes an inductive element (e.g., a transformer) instead of a capacitor, so that the current-to-be-applied to a patient's skin can be controlled. In conventional devices that utilize a capacitor for their electrical pulse generator, when that capacitor is coupled to a patient's skin, the resultant circuit amounts to a first capacitor (that being the capacitor of the pulse generator) in parallel with a second capacitor (that being the capacitor due to the capacitive/resistive effect of a skin operating as a load). When a voltage is applied to the skin by way of an electrical pulse, the discharge of a voltage from the first capacitor to the second capacitor results in a very large current spike for an initial short period of time, whereby that large current spike cannot be readily controlled. This can result in negative effects to the patient's skin caused by the large current spike. By utilizing an inductive element (e.g., a transformer) instead of a capacitive element in the pulse generator, as shown in FIG. 4 of the drawings, no current spike results when a probe with electrodes providing electrical pulses is coupled to a patient's skin (since the "capacitive skin" smoothly receives the current and voltage from the "inductive pulse generator").

Figure 4:
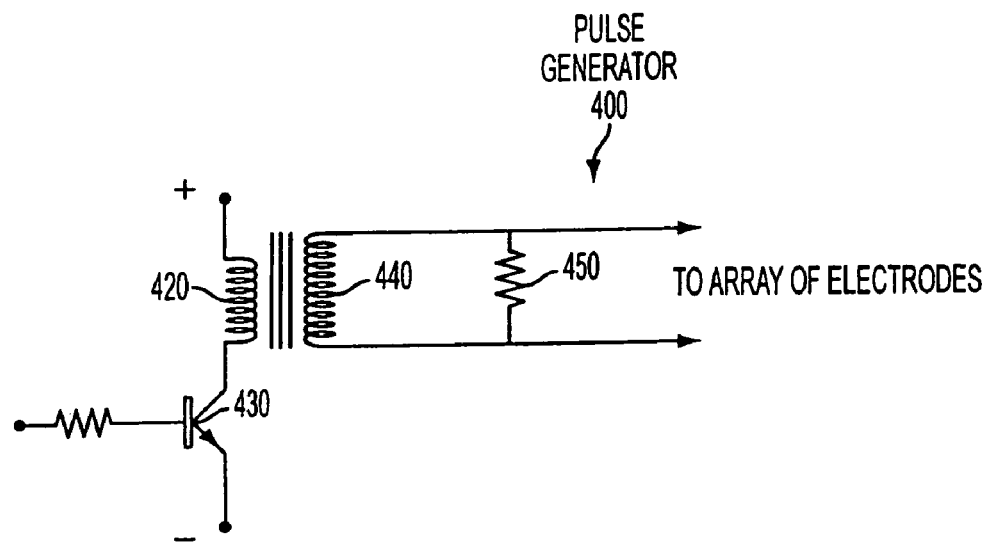
FIG. 4 shows an electrical diagram of a pulse generator that provides electrical pulses to an array of electrodes disposed on a vibrating plate provided at a head-end of the probe, according to one possible configuration of an apparatus according to the invention.
Figure 4A:
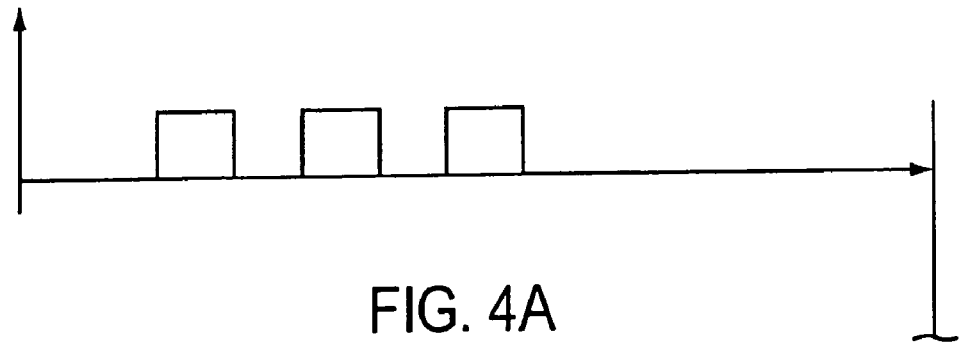
FIG. 4A shows a train of square-wave pulses that are input to the pulse generator of FIG. 4.
Figure 4B:
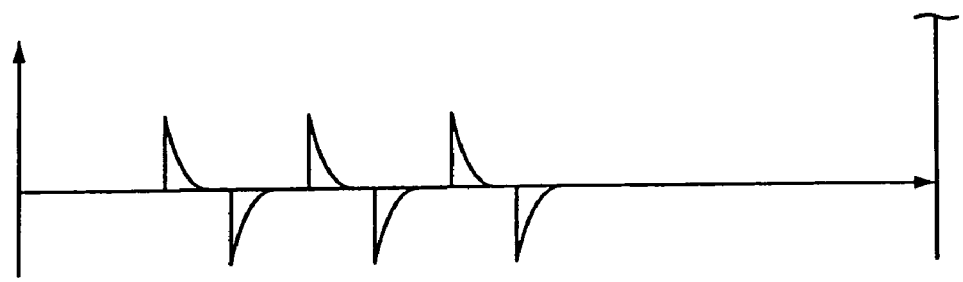
FIG. 4B shows a train of exponential pulses that are output from the pulse generator of FIG. 4.
Figure 5:
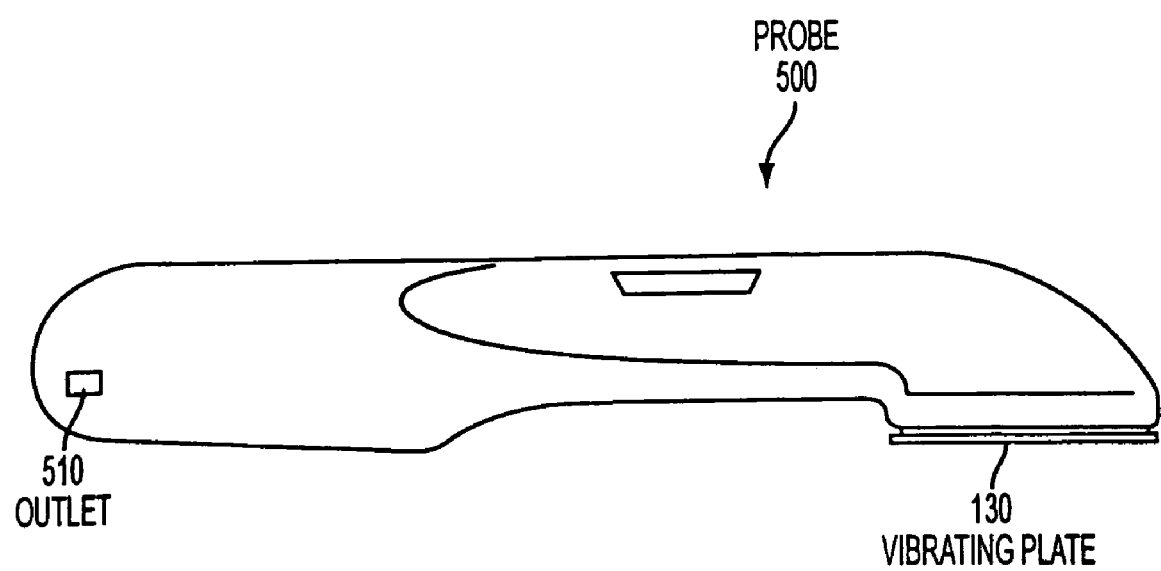
FIG. 5 shows one configuration of a hand-held probe that is used to provide both electrical and mechanical stimulation to the skin, according to one or more embodiments of the invention.

Switching transistor 430 provides square-wave pulses as shown in FIG. 4A to the primary winding of the transformer 410, as shown in FIG. 4. The pulses generated by the pulse generator 400 of FIG. 4, when the load is a pure resistance (or inductive or other type of reactive load), is a sequence of exponential decay pulses of opposite symmetrical polarities, as shown in FIG. 4B. Such a circuit that includes the pulse generator 400 provides an excellent coupling to the impedance of the skin. Moreover, in addition to the current control described above, the inductance of the transformer 410 together with the capacitance of the skin generates a resonant circuit, which is desirable to achieve an opening of the skin pores or membranes.

The voltage waveform is conveniently modified when applied to the skin due to the fact that the electrical equivalent circuit of the skin is a resistance and a capacitance in parallel. The resulting voltage waveform has a longer rise time (due to the RC time constant), and is dependent upon the capacitance of the skin, while maintaining the same peak current and the same exponential decay waveform.

Such a circuit according to the first embodiment gives an advantage in comparison to traditional pulse generators that deliver pulses of a predefined value and shape of tension or current. By way of the present invention according to the first embodiment, it is possible to deliver higher energy value per pulse, and also at the same time avoid possible damage to the skin that would occur if high current amounts were applied to the skin. The circuit utilized in the first embodiment self adjusts the value of the current, voltage and waveform shape. In particular, the impedance of the skin decreases after the first pulse is applied to the skin. In this way, the voltage of the first pulse is higher than subsequent pulses, since the impedance of the skin is higher at the time the first pulse is applied to the skin. The voltage of the second and following pulses applied to the skin decreases with the decreasing of the impedance of the skin, while maintaining the peak current at the same or almost the same value.

Typical values of current and voltage are provided herein. Case 1: load impedance of 10 kohm, peak voltage of 100 V, peak current of 10 milliamperes, pulse width of 220 microseconds. Case 2: load impedance of 1 kohm, peak voltage of 10 V, peak current of 10 milliamperes, pulse width of 220 microseconds. The pulses are preferably delivered in bursts, where the burst rate is the same or nearly the same as the mechanical vibration rate. A typical value of the burst rate (and mechanical rate) is between 40 Hz and 100 Hz.

The inventor of this application has also realized that the use of mechanical vibrations at the same time that the electrical pulses are applied to skin, and at a same or nearly the same frequency as the burst pulse rate, results in a patient having a greater tolerance to the strength (current and voltage) of the electrical pulses applied to the patient's skin. For example, using a electrical pulse burst rate of 50 Hz (that is the rate between bursts of pulses), mechanical vibrations may be provided at a range of between 40 to 60 Hz at the same time that the electrical pulse bursts are applied to the skin, to provide a "masking effect." The inventor has also found that utilizing mechanical vibrations at or around (e.g., +/−10% of) the fundamental frequency of the electrical pulse burst rate, at or around the first harmonic of the electrical pulse burst rate, at or around the second harmonic of the electrical pulse burst rate, and/or at or around the third harmonic of the electrical pulse burst rate, gives the patient a "good sensation" so that he/she can tolerate a higher strength of electrical pulses being applied to his/her skin at the same time. Thus, for a 50 Hz electrical pulse burst rate, mechanical vibrations may be applied to the patient's skin at the same time, with the mechanical vibration rate being either 40 to 60 Hz, 90 to 110 Hz, 140 to 160 Hz, and/or 190 to 210 Hz. By having mechanical vibrations applied to the patient's skin at the same time that the electrical pulse bursts are applied to patient's skin, the patient's discomfort level caused by the tinging sensation of the electrical pulses is lessened (e.g., masked somewhat).

Normally, when a square wave is applied to the skin, due to the capacitive effect of the skin, it is possible to obtain about a three microsecond time constant exponential decay current. This is what happens when a square wave voltage is applied to a circuit that corresponds to a resistor in parallel with a capacitor.

With such a circuit, only the peak current is enhanced, charging to a maximum allowable voltage the skin capacitance by applying an electrical energy equal to the magnetic energy of the transformer 410. This effect most likely provides for the opening of the cell membranes or pores of the skin (to achieve the transpiration effect) only during the time when each pulse is applied to the skin.

The effect of applying the probe to the skin is that the skin vibrates due to the electrical pulses applied by way of the array of electrodes. The electrical pulses are preferably applied at a fixed frequency between 200 and 10,000 Hz (optimally at a frequency value between 2,500 to 3,000 Hz), and are grouped in burst of pulses (e.g., each burst may correspond to 100 to 1000 separate pulses that have opposite polarities with respect to adjacent pulses in the same burst of pulses). The ON time of each burst is a fixed value between 5 to 50 milliseconds, and the OFF time between two consecutive bursts is a fixed value between 5 to 50 milliseconds (the preferred burst ON time is 10 milliseconds and the preferred OFF time between consecutive bursts is 10 milliseconds).

As described above, the electrical pulses applied to the skin by way of the electrodes are preferably exponential pulses with peak-to-peak voltage of 160 V at a fixed frequency between 2,500 to 3,000 Hz. One way of providing such electrical pulses is by an electrical structure that corresponds to a pulse generator 400 as shown in FIG. 4, in which a transformer 410 is used as an element of the pulse generator 400.

The transformer 410, as well as the other elements of the pulse generator 400, are preferably housed within the probe 500 of FIG. 5.

Referring back to FIG. 4, the primary winding 420 of the transformer 410 is driven by a transistor 430 that is switched on and off, and the secondary winding 440 of the transformer 410 is directly applied to the array of electrodes (see FIG. 1A or 1B) with an electrical resistance 450 provided therebetween. The electrical resistance 450 may be 200 Kohm or some value in that range (e.g., 100 Kohm to 500 Kohm), and is provided in order to avoid high voltages when the array of electrodes are not applied to the skin, so that in that case it operates as an open circuit. In such a situation, the peak-to-peak voltage is 400 V or thereabouts.

Along with the electrical pulses applied to the skin, a mechanical vibration is also provided to the skin in the first embodiment in order to increase the absorption of a substance that is applied on the skin.

The absorption effect is enhanced by the simultaneous increase of transpiration, whereby the absorption effect is greatest when the mechanical vibration is synchronized in phase and in frequency with the electric pulse application. Thus, in the example discussed above, while the electrical burst of pulses (at 2,200 Hz) are provided to the skin at a burst ON/OFF frequency, e.g., 50 Hz, by way of an electrode array, the skin is also mechanically vibrated at the same frequency, e.g., 50 Hz, by way of the vibrating plate. The mechanical vibration and the electrical burst application are also preferably provided in phase with respect to each other, in order to increase the skin absorption effect. There are several well known ways to achieve this frequency and phase synchronization. In the preferred embodiments described herein, an optical sensor (not shown) detects the movement of the eccentric of a motor that is used to provide the mechanical vibrations (see FIGS. 1A and 1B, for example), and gates the burst of electrical pulses based on the detected movement.

Thus, in the example discussed above, while the burst of electrical pulses are provided to the skin by way of the electrode array, the skin is also mechanically vibrated at the same frequency by way of the vibrating plate. The mechanical vibration and electrical pulse application is also preferably provided in phase with respect to each other, in order to increase the skin absorption effect.

Moreover, the absorption effect is further enhanced when the mechanical vibration is applied orthogonal to the surface of the skin. While Applicant does not intend to be tied down to any particular theory of operation, one possible explanation of the physical phenomena of one or more embodiments of the present invention is that, while the electrical pulses "stretch" the skin, thus increasing periodically the diameter of the pores of the skin, at the same time the mechanical vibration "pumps" the substances (gel, liquid or cream) inside the skin (through the opened pores). The mechanical and electrical synchronization achieves the effect that the "pumping" action (due to the mechanical stimulation of the skin) takes place at the same instant in time that the pores are at their maximum "open" diameter (due to the electrical stimulation of the skin).

The apparatus according to a first embodiment the present invention includes a probe having two main parts:

A) a handle containing a power source (e.g., batteries) and a pulse generator; and B) a vibrating head containing components for generating the vibration and also containing an array of electrodes.

The vibrating head, in a preferred configuration of the first embodiment, includes a D.C. electrical motor for generating vibrations to the skin. FIGS. 1A and 1B show two different views of the D.C. electrical motor 110, the rotating shaft of the D.C. electrical motor 110 is an eccentric 120 to thereby provide eccentric motion. The eccentric motion, during rotation of the D.C. electrical motor 110, generates a vibration onto the vibrating plate 130 (that is directly coupled to the D.C. electrical motor 110) that is at the same frequency of the rotation of the D.C. electrical motor 110 (e.g., 50 Hz or 60 Hz or some other desired frequency). Other ways of causing vibrations in synchronization with the providing of electrical pulses to a patient may be contemplated while remaining within the scope of the invention. Note that the use of mechanical pulses at the same or nearly the same rate as bursts of electrical pulses, but not necessarily in synchronism with each other, as described earlier, provides a good effect in that it lessens the patient's discomfort level associated with the buzzing and tinging sensation caused by receiving electrical pulses to the skin alone. Also, the use of adjacent pulses in each burst of opposite polarity to each other results in no current buildup to the patient's skin, which can be a detrimental effect of conventional devices that use electrical pulses of the same polarity to be provided to a patient's skin.

As explained earlier, FIG. 4 shows circuitry for providing electrical pulses to the array of electrodes shown in FIGS. 2A and 2B. The circuitry of FIG. 4 corresponds to a pulse generator 400, and is preferably disposed within the housing of the probe 500 of FIG. 5. The electrical pulses generated by the pulse generator 400, when those pulses are provided to the skin, preferably are exponential pulses with peak-to-peak voltage of 160 V at a frequency of between 2,500 Hz to 3,000 Hz. Of course, other peak-to-peak voltage values (e.g., 100 V to 200 V) and operating frequencies (50 Hz to 15,000 Hz) may be employed, while remaining within the scope of the invention as described herein. Alternatively, sawtooth or sinusoidal pulses may be provided to the electrodes, but exponential pulses appear to provide better skin transpiration results.

FIGS. 1A and 1B show the vibrating plate 130 that is physically coupled to the D.C. electrical motor 110. The vibrating plate 130 preferably is 50×50 mm in size (other sizes are possible while remaining within the scope of the invention), where parallel metallic stripes are deposited on it as shown in FIG. 2A, in order form the array of electrodes. The vibrating plate 130 is caused to vibrate at the same phase and frequency as the electrical pulses provided to the skin by way of the array of electrodes (disposed on the vibrating plate), in order to enhance the skin absorption effect.

As shown in FIG. 2A, which shows a first embodiment of an electrode array 210 that is provided on a skin-side surface of the vibrating plate 130, five parallel metallic stripes 220 are provided, each preferably of a size of 50 mm×4 mm. Each of the five electrodes 220 are preferably 6 mm apart from adjacently-positioned electrodes. The electrodes 220 are alternately electrically connected (e.g., the first, third and fifth row are electrically connected to each other by way of electrical line 250; and the second and fourth rows are electrically connected to each other by way of electrical line 260). Other electrode array configurations are possible while remaining within the scope of the invention, such having a number of electrodes greater than two, such as having seven or eight electrodes.

FIG. 2B shows a second embodiment of an electrode array that is provided on a skin-side surface of a vibration plate. In FIG. 2B, there are provided 25 round electrodes 230 each of 4 mm diameter, each separated at least 6 mm from adjacently-positioned round electrodes. The round electrodes 230 are alternately electrically connected to each other (e.g., the electrodes on the first, third and fifth rows are electrically connected to each other by way of electrical line 270; and the electrodes on the second and fourth rows are electrically connected to each other by way of electrical line 280). The spacing between the electrodes 230 shown in FIG. 2B may vary between 1 to 20 mm and the size of each of the electrodes 230 may vary between 1 to 20 mm in diameter.

FIG. 2C shows an array of electrodes provided on an outer surface of the vibration plate that faces the skin, according to the third embodiment of the invention. In FIG. 2C, there are provided electrodes 233 that are disposed on the periphery of the vibration plate, which are electrically coupled to each other, and which are electrically coupled to a first output of the pulse generator 400 by way of a first electrical connection 235. In FIG. 2C, there is also provided a centrally-positioned electrode 237, which is not electrically coupled to any other of the electrodes, and which is electrically coupled to a second output of the pulse generator 400 by way of a second electrical connection 239.

Figure 3:
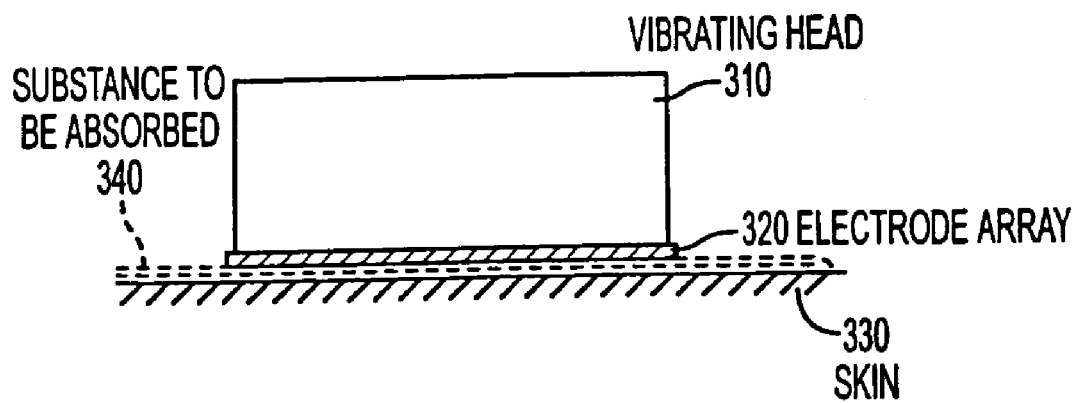
FIG. 3 shows a side view of a head of a probe that is used to provide both electrical and mechanical stimulation to the skin, in order to have a substance previously applied to the skin to be absorbed better, according to the invention.

FIG. 3 shows a side view of a vibrating head 310 of a probe that is used to provide both electrical and mechanical stimulation to the skin according to an embodiment of the present invention, in order to have a substance previously applied to the skin be absorbed better. As shown in FIG. 3, the vibrating head 310 includes the array of electrodes 320 provided on a skin-side surface thereof. The array of electrodes 320 may be provided in a manner such as shown in either FIG. 2A or 2B, for example. Between the array of electrodes 320 and the skin 330 there is provided a substance 340 to be absorbed, whereby the substance 340 has been previously applied to the skin 330 (e.g., applied to the skin between 30 seconds to 2 minutes before the probe is to be applied to the skin 330). Application of mechanical vibrations and electrical pulses enhances the absorption of the substance 340 into the skin 330.

FIG. 5 shows one configuration of a hand-held probe 500 that may be used to provide both electrical and mechanical stimulation to the skin, according to one or more embodiments of the invention. The probe 500 is configured to be readily held by one hand of a user. A bottom portion of the probe 500, at which a user's hand is gripped thereon to thereby hold the probe 500, may include an outlet 510 for coupling an electrical cable to an electrical outlet (e.g., wall outlet), so as to provide A.C. voltage to the probe 500 in that manner. Alternatively, battery power may be used, by way of batteries (not shown) disposed within the housing of the probe 500. Battery power may be utilized when A.C. power is not readily available. Also, the pulse generator 400 of FIG. 4 is preferably housed at the handle portion of the probe 500.

The head portion of the probe 500 is where the vibrating plate 130 (see FIG. 1A or 1B) is provided, and also where the D.C. electrical motor 110 (see also FIG. 1A or 1B) that provides the mechanical vibrations to the vibrating plate 130 is preferably provided housed within. The array of electrodes (see FIG. 2A or 2B) are provided on an outer surface of the vibrating plate 130, thereby facing the skin of a user to be treated with the probe 500.

A typical application time of the probe to the skin may be on the order to 10s of seconds up to several minutes.

Figure 6:
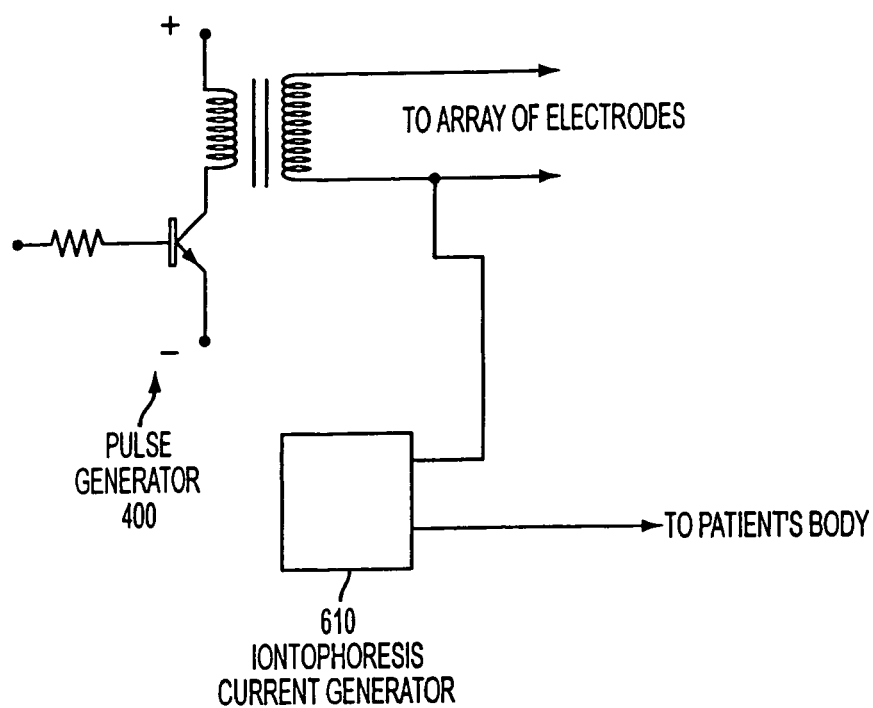
FIG. 6 shows a current generator connection according to a fourth embodiment of the invention.

In a fourth embodiment, as shown in FIG. 6, the output of the pulse generator 400 (see also FIG. 4) is connected to a D.C. current generator 610, which induces a iontophoresis effect in addition to the previously described skin absorption/transpiration effects. The iontophoresis effect is well known to those skilled in the art, and several ionthophoresis electrical generators are currently available in the market, either D.C. or D.C. pulsed. A D.C. current output by the D.C. current generator 610 is applied between the electrodes of the probe and a ground plate that is connected with the patient's body. Depending on the substance to be absorbed into the patient's skin, the patient ground plate connection is coupled to either the positive or the negative of the D.C. current generator 610, in a manner known to those skilled in the art. Instead of using continuous D.C. current, there can alternatively be provided D.C. current pulses that have the same average current value as the continuous D.C. current case, and which have a duty cycle between 5 and 50% and a frequency between 10 and 5000 Hz. In such a case, the peak current of the D.C. current pulses is higher during the pulsed (ON) times.

Figure 7:
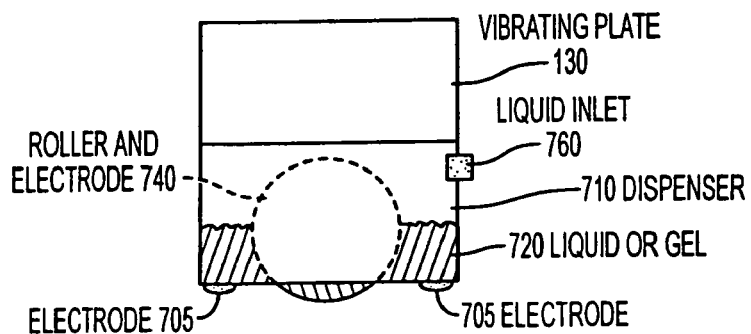
FIG. 7 shows elements provided at the head portion of a probe, according to a fifth embodiment of the invention.
Figure 8:
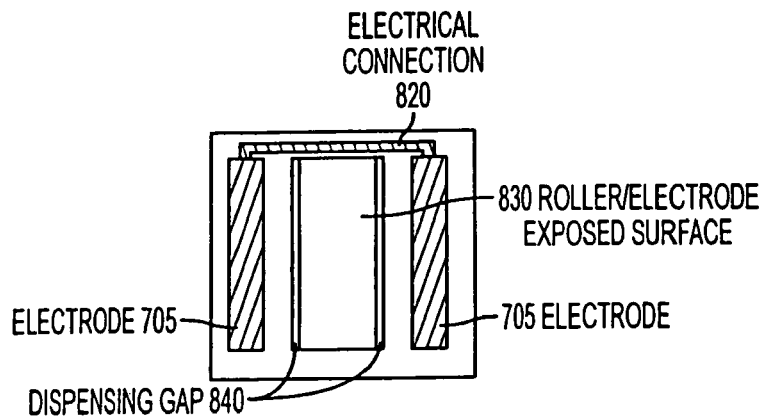
FIG. 8 shows a front view of the head portion of the probe according to the fifth embodiment of the invention.

In a fifth embodiment, as shown in FIGS. 7 and 8, a dispenser or chamber 710, which is configured to hold liquid or cream or gel 720, is integrated in the vibrating head of the probe. The dispenser or chamber 710 is provided between an array of electrodes 705 and the vibrating plate 130. The burst of electrical pulses are applied by way of a conductive roller 740 that dispenses the liquid, and by the array of electrodes 705. A D.C. current as in the third embodiment can also be added between the array of electrodes 705 and the patient's body, to induce a iontophoresis effect as well. While the vibrating head is moved on the patient's skin, the roller 740 delivers the liquid or cream or gel 720 to the patient's skin.

The chamber 710 in which the roller 740 is disposed in the vibrating head can be filled with a liquid, cream or gel substance 720 by way of a removable cap (not shown). In particular, the cap is removed (e.g., screwed off of the head of the probe), and then a user fills the chamber 710, through the liquid inlet 760, with the substance 720 to be provided to the patient's skin. The user then closes the cap (e.g., screws it back onto the liquid inlet 760) to thereby keep the substance 720 within the chamber 710 of the probe until it is ready to be applied to the patient's skin by way of the roller 740.

FIG. 8 shows a front view of the electrodes 705, which are shown as two stripe electrodes that are electrically connected to each other by way of electrical connection 820. Of course, other types of electrode arrays, such as those shown in FIGS. 2A and 2B, can alternatively be used in this fifth embodiment. The exposed surface 830 of the roller 740 that applies the substance to the patient's skin, is shown in FIG. 8. Dispensing gaps 840 are also shown in FIG. 8, whereby these gaps 840 allow the liquid, cream or gel substance 720 in the chamber 710 to gradually come out of the chamber 710 and thereby be applied to the patient's skin by way of the roller 740.

In a sixth embodiment of the invention, an apparatus for enhancing absorption of the skin includes an array of electrodes, and a pulse generator that is electrically coupled to the array of electrodes. The disposition of the array of electrodes may be any of the dispositions shown in FIGS. 2A-2C, for example. In a preferred implementation of the sixth embodiment, electrical pulses outputted by the pulse generator 400 to the array of electrodes are a sequence of exponential pulses, such as the pulse train shown in FIG. 4B. The exponential electrical pulses are applied to the skin by way of the array of electrodes and are generated by the secondary winding of a high voltage transformer with the primary winding driven by a square wave voltage, as seen by FIGS. 4, 4A and 4B.

In the sixth embodiment, unlike the previous embodiments, a vibrating head is not utilized, but rather skin absorption enhancement is obtained just by the providing of the electrical pulses to the skin by way of the array of electrodes. The array of electrodes according to the sixth embodiment are provided on a plate at the head of the probe, whereby the head and the plate do not vibrate. Thus, in the sixth embodiment, the structure as shown in FIGS. 1A and 1B would not be utilized, but rather just a plate for holding the electrodes in place at the head of the probe would be needed.

In a seventh embodiment, a vibrating head is utilized, as in the first through fifth embodiments, but where the vibrating head is capable of being turned on or off, by way of a control (e.g., switch) provided on the probe. The control can readily be manipulated by an operator of the probe, in order to treat a patient.

Figure 9:
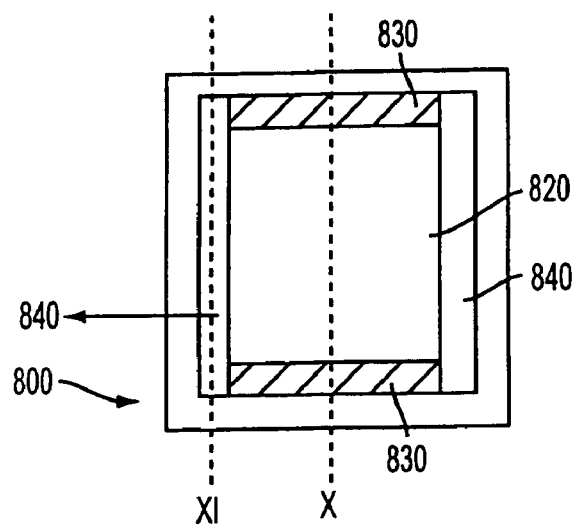
FIG. 9 shows a front view of the head portion of the probe according to an eighth embodiment of the invention.
Figure 10:
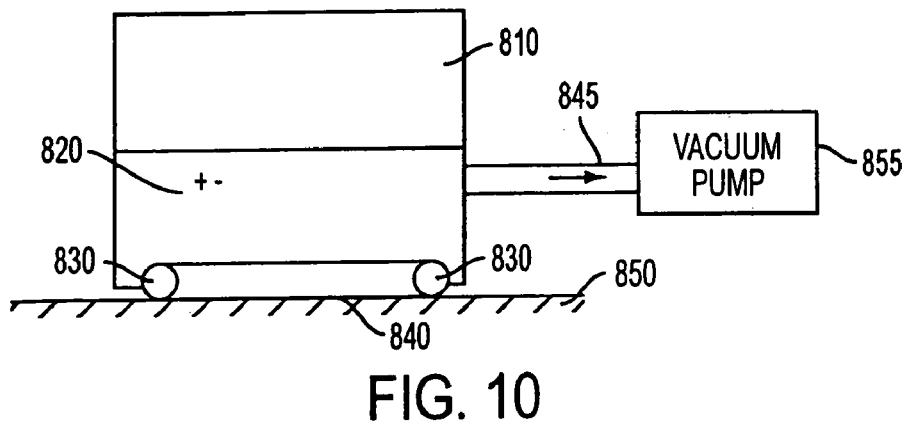
FIG. 10 shows a first section view of the head portion of the probe according to the eighth embodiment of the invention, whereby suction is not being applied to the skin.
Figure 11:
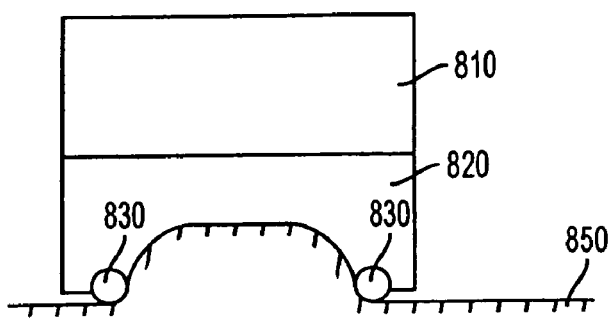
FIG. 11 shows a second section view of the head portion of the probe according to the eighth embodiment of the invention, in which suction is being applied to the skin.

An eighth embodiment of the invention is described below, with reference to FIGS. 9-11. FIG. 9 shows a front view of a head 800 of a probe, whereby that view shows the portion of the probe that is applied to the skin of a patient. FIG. 10 shows a section view taken along an axis of one belt, and FIG. 11 shows a section view taken at the middle of the head of the probe.

The eighth embodiment provides for a fairly even absorption under the skin of a substance previously applied to the skin, such as collagen previously applied to the skin. In the eighth embodiment, a head 800 of a probe to be applied to the skin includes a vibrating plate 810, a vacuum chamber 820, rollers 830, and belts 840 disposed around the rollers 830. The rollers 830 are conductive rollers, whereby the rollers 830 are electrically coupled to electrodes (see FIGS. 2A through 2C, for example) provided on the vibrating plate 810. As in the other embodiments, a pulse generator (see FIG. 4, for example) is electrically coupled to the electrodes on the vibrating plate 810, in order to provide electrical pulses to the patient's skin (by way of the conductive rollers).

In the eighth embodiment, the rollers 830 are separated from each other by around 40 mm. Of course, other separation distances are possible, while remaining within the scope of the invention (e.g., 20 mm to 80 mm separation). The rollers 830 are disposed at one end of the vacuum chamber 820, whereby the vacuum chamber 820 includes an opening that is coupled to a pipe 845 that is in turn coupled to a vacuum pump 855.

When the vacuum pump 855 is operated, the vacuum chamber 820 generates a suction effect on the skin 850, thereby enabling a stronger contact between the rollers 830 and the skin 850, and thereby generating an additional massaging effect to the skin 850, in addition to the vibrations generated by the vibrating plate 810. On opposite ends of the rollers 830 are the belts 840, which are preferably rubber belts. The belts 840 are used in order to avoid direct friction between the skin 850 and the body of the vacuum chamber 820.

The eighth embodiment provides good skin absorption results and decreases the appearance of cellulite on the skin after application of a substance for reducing cellulite is applied to the skin. Such a substance for reducing cellulite that can be applied to the skin may be jarulon acid, for example. Such a substance could also be previously spread on the skin and absorbed by the skin utilizing one of the previously-described embodiments.

Also, while the eighth embodiment has been described as having a vibrating plate, as in the first through fifth embodiments, a non-vibrating plate as in the sixth and seventh embodiments (when the vibrating plate is turned off) may be utilized in an alternative configuration. In that case, the plate disposed above the vacuum chamber is non-vibrating, and contains electrodes disposed therein.

A ninth embodiment of the invention will be described in detail hereinbelow with reference to FIGS. 12-14. The ninth embodiment includes a motor 1, a screw 2, a slide 3, a frame 4, a piston 5, a syringe 6, a pipe (or tubing) 7, a central electrode 8, and circumferential electrodes 9 (that are disposed outside of the central electrode 8) on a head 10. The head 10 is a head portion of a probe, such a probe shown in FIG. 5 in the previous embodiments (except for the fifth embodiment, whereby the substance is disposed within a chamber within the head that is adjacent to the electrode plate, and thus a syringe would not be needed in that case), for example.

Figure 12:
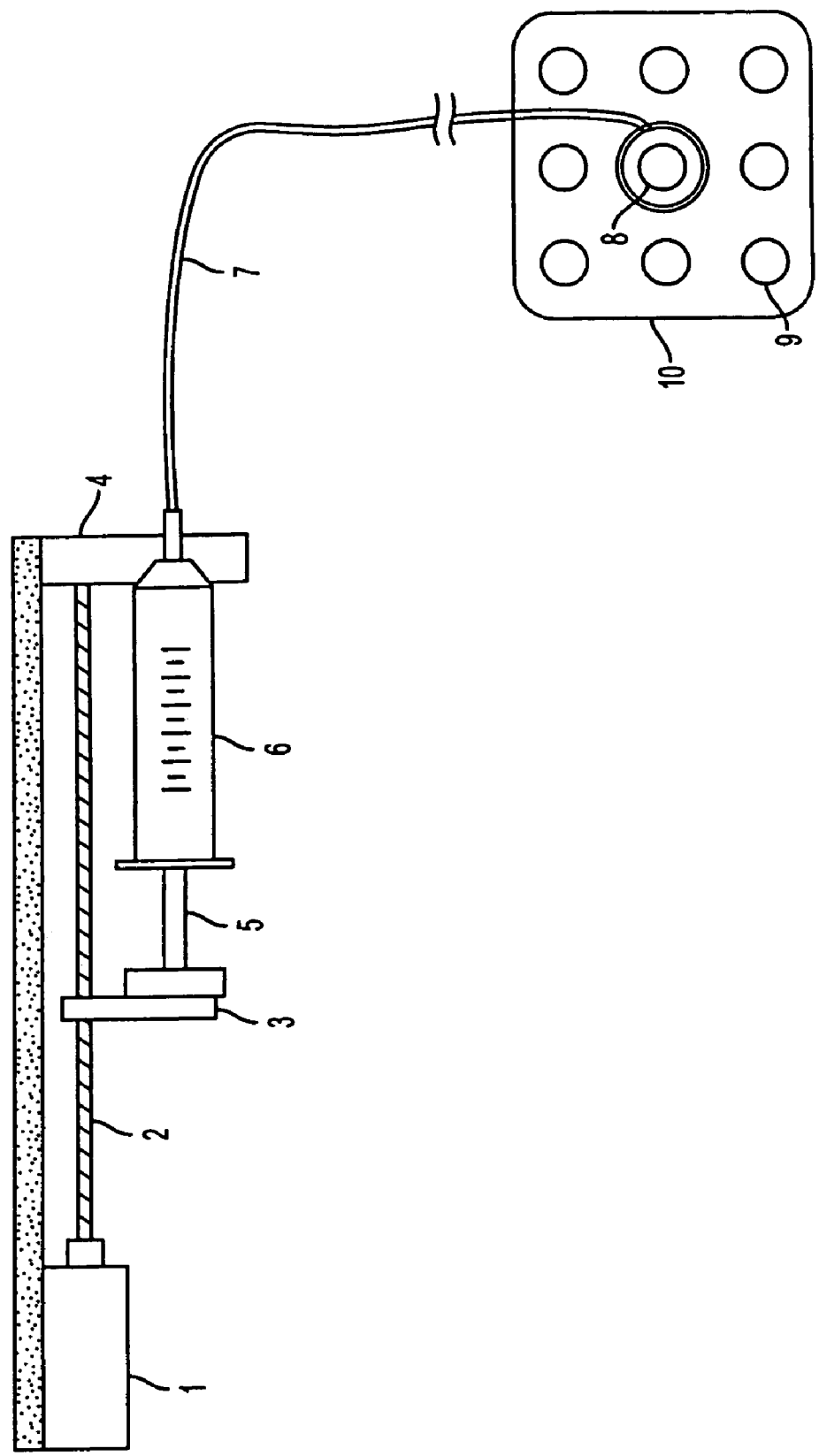
FIG. 12 shows a structure of an electroporation device according to a ninth embodiment of the invention.

In the ninth embodiment, the syringe 6 is preferably a disposable, single-use syringe, which is positioned adjacent to the probe (only the head 10 of the probe is shown in FIG. 12, whereby the rest of the probe is hidden behind the head 10 in the view provided in FIG. 12). The syringe 6 is inserted or fitted onto the frame 4, and does not move relative to the frame 4. For example, the frame 4 may be placed on a table next to a bed on which a patient to be treated is located.

The piston 5 is operable to move relative to the frame 4, whereby the movement is caused by the motor 1, the screw 2, and the slide 3, which operate together as a moving means. With the configuration shown in FIG. 12, the probe is free-standing and can be moved a certain amount (e.g., 1 to 10 feet, depending on the length of the tube 7) relative to the frame 4 (while maintaining a coupling to the syringe 6 by way of the tube 7 that couples the syringe 6 with the head 10 of the probe). That way, the probe can be moved around to treat different areas of a skin of a patient lying on a bed, while the frame containing the syringe 6 rests in place on a table next to the bed. In an alternative configuration, the probe and the syringe 6 can both be mounted on the frame 4, as a single-block construction. In this configuration, the entire frame is moved to different areas of the patient's skin, to thereby treat the patient by way of a probe that is inserted in the frame. The head of the probe extends out from one end of the frame, so that it can be placed against the patient's skin.

In a preferred implementation, the motor 1 is powered by a different power source than the source providing power to the probe. However, in a different implementation, the motor 1 and the probe may be powered by the same power source.

A tube or pipe 7 is used to connect the syringe 6 with the head 10 of the probe. The tube 7 is preferably a disposable, single-use component, and may be a flexible plastic tubing, for example. The head 10 is preferably a vibrating head, such as described earlier with respect to other embodiments. In an alternative configuration, the head 10 does not vibrate, and only electrical pulses are provided to the skin (so as to electroporate the skin to thereby absorb the substance provided to the skin by way of the syringe 6 and tube 7) in this alternative configuration. The tube 7 is preferably 0.5 to 3 millimeters in diameter, and is sized so as to allow a liquid or cream-like substance to flow through the tube 7, and exit the tube 7 at a second end opposite a first end of the tube 7 that is coupled to the syringe 6. Such a substance to be applied to the skin may include water-based collagen, water-based elastine, and anesthetic, or other type of drug, just to name a few.

Figure 14:
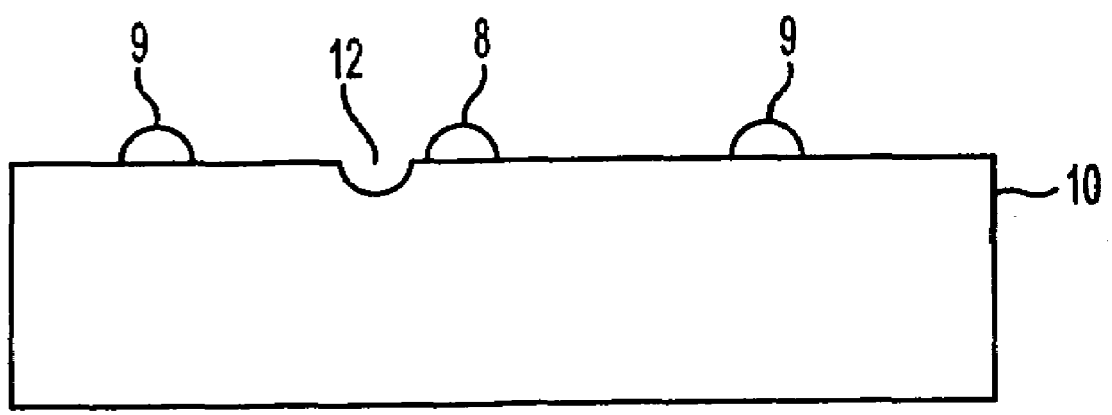
FIG. 14 shows a side view of the head of a probe used in an apparatus according to the ninth embodiment of the invention.

Referring now to FIG. 14, the tube 7 couples to the head 10 by way of a groove 12 that is located at an end of the head 10 and that is provided all the way to a groove 11 that surrounds the central electrode 8. The groove 12 is sized so as to accept the tube 7 fitted therein to provide a snug fit, whereby the tube 7 is preferably fitted within the groove 12 by feeding the tube 7 within the groove 12 from the end of the head 10 where one end of the groove 12 is disposed. In the ninth embodiment, the size of the groove 12 is such that the tube 7 does not extend above the upper surface of the head 10 (where the electrodes 8, 9 are disposed), or whereby the tube 7 extends slightly below the upper surface (plate) of the head 10. That way, the tube 7 will not be felt by the patient when the head 10 of the probe is moved along the skin of the patient during a treatment. Preferably, the tube 7 will not be in contact with the skin of the patient during treatment of the patient by way of a method and/or apparatus according to the ninth embodiment. The top surface of the head 10 preferably has a plate-like configuration, so as to provide a smooth feeling to the patient's skin.

On the top surface of the head 10 there are provided one central electrode 8 and a plurality of circumferential electrodes 9 disposed around the central electrode 8. The groove or trough 11 surrounding the central electrode 8 is preferably 1 mm wide, whereby the groove 11 is coupled to one end of the groove 12 in which a portion of the tube 7 is disposed. That way, when a substance is flowed out of the syringe 6 (by way of action by the motor 1, the screw 2 and the slide 3), the substance flows through the tube 7 (disposed within the groove 12) and thereby into the groove 11. The substance collects within the groove 11 surrounding the central electrode 8, and is absorbed by the skin during an electroporation treatment (using electrical pulses and mechanical vibrations) by way of the ninth embodiment. When the top surface (plate) of the head 10 is placed in contact with the patient's skin, the substance within the groove 11 comes into contact with the patient's skin, and is absorbed by the skin.

Although eight circumferential electrodes 9 are shown in FIG. 12, the invention according to the ninth embodiment can operate with different numbers of circumferential electrodes 9. For example, a minimum of two circumferential electrodes 9, disposed opposite from each other (with the central electrode 8 disposed therebetween), may be utilized in a different configuration. Also, four circumferential electrodes 9 and more than eight circumferential electrodes 9 may be utilized in other different configurations (e.g., 16 electrodes, 32 electrodes, or an odd number, such as three, five, or seven, circumferential electrodes surrounding the central electrode 8) of the ninth embodiment.

A pulse generator, such as the one shown in FIG. 4 (see also FIGS. 4A and 4B), is used to provide electrical pulses to the electrodes 8, 9 disposed on the head 10 of the probe. As explained earlier, the preferred shape of the electrical pulses is an exponential shape, as shown in FIG. 4B. Alternatively, sinusoidal or sawtooth waveforms may be provided, but exponential pulses provide a better skin transpiration effect. Operation of the pulse generator that may be utilized in the ninth embodiment has been described in detail with respect to the first embodiment described previously, and will not be described here for sake of brevity.

One of the two outputs of the pulse generator (see FIG. 4) is connected to the central electrode 8, and the other of the two outputs of the pulse generator is connected to one of the circumferential electrodes 9. The circumferential electrodes 9 are coupled to each other electrically on the back side of the head (see dashed line in FIG. 2C), so that each of the electrical pulses provided on the other of the two outputs of the pulse generator is provided to all of the circumferential electrodes 9 simultaneously.

The voltage of the electrical pulses provided to the skin from each of the eight circumferential electrodes 9 can be considered as a "ground" with respect to the voltage of the electrical pulse provided to the skin from the one central electrode 8. Since the central electrode 8 carries more electrical current than each of the eight circumferential electrodes 9, the circumferential electrodes 9 act like a ground connection, whereby the electrical current carried by each of the eight circumferential electrodes 9 is approximately eight times less than the electrical current carried by the central electrode 8.

The piston 5 of the syringe 6 is moved by the motor 1, which is a DC electric motor in a preferred implementation. The motor 1 is connected to the screw 2, which moves the piston 5 by way of the slide 3 that is attached to the screw 2 at a particular location on the screw 2. When the head 10 of the probe is positioned on a patient's skin, electrical pulses are delivered to the electrodes 8, 9, and the piston 5 of the syringe 6 is moved by the motor 1 in order to deliver the liquid or cream-like substance (or drug) from within the syringe 6 to the patient's skin. The liquid, cream or drug is preferably provided to the patient's skin in a slow, controlled manner, to allow the substance to be properly absorbed within the skin. For example, a water-based collagen, a water-based elastine, an anesthetic, or other type of drug may be provided within the syringe 6, to then be provided to the skin of a patient (to be absorbed therein) by way of the method and apparatus according to the ninth embodiment.

The enhancement of the skin absorption by electrical pulses applied to the skin, and also by mechanical vibrations applied to the skin at the same time in a synchronous manner (see description of the vibrating plate with respect to other embodiments) of the ninth embodiment, enables the absorption of a drug or other type of substance delivered by way of the syringe 6. A typical drug absorption quantity is 1 cubic centimeter in one to five minutes, by using the method and apparatus according to the ninth embodiment. In this regard, the timing of the movement of the piston 5 is such that the correct amount of substance is output from the syringe 6 during a treatment of a patient, whereby when the probe is turned on, this event will provide a trigger signal to the motor 1 to start to operate. Operation of the motor 1 will in turn cause the substance within the syringe 6 to be pushed out of the syringe 6, and into the groove 12 surrounding the central electrode 8.

The substance is introduced within the syringe at a previous time, so that the syringe 6 with the substance provided therein can then be attached to the frame 4, coupled to the tube 7, and thereby provide an apparatus that can introduce drugs and/or other substances to the skin of a patient, by way of a probe having a head 10 with electrodes 8, 9 provided on an outer surface or plate of the head 10. As explained earlier, the head 10 vibrates, so that both electrical and mechanical vibrations are provided to the patient's skin at a same time the drug or other substance is provided to the patient's skin (by way of the substance disposed within the trough or groove 12 being in contact with the patient's skin during a treatment of the patient). In an alternative configuration, which provides a skin transpiration effect not as good as using both mechanical vibrations and electrical pulses, only electrical pulses are provided to a patient's skin (the head does not vibrate). This configuration is cheaper to build, and may be suitable for certain instances.

The motor 1, screw 2, slide 3, piston 5, syringe 6, frame 4 and tube 7 may be coupled to different types of probes, in order to provide an apparatus for skin absorption enhancement and transdermal drug delivery. For example, any of the probes described with respect to the other embodiments (except those that have the substance stored in a container within the head of the probe) may be utilized with the components described above. Also, the structure for moving a substance out of the syringe 6 may be accomplished by ways other than the screw/slide/motor "moving means" described with respect to FIG. 12, while remaining within the scope of the invention.

Figure 13:
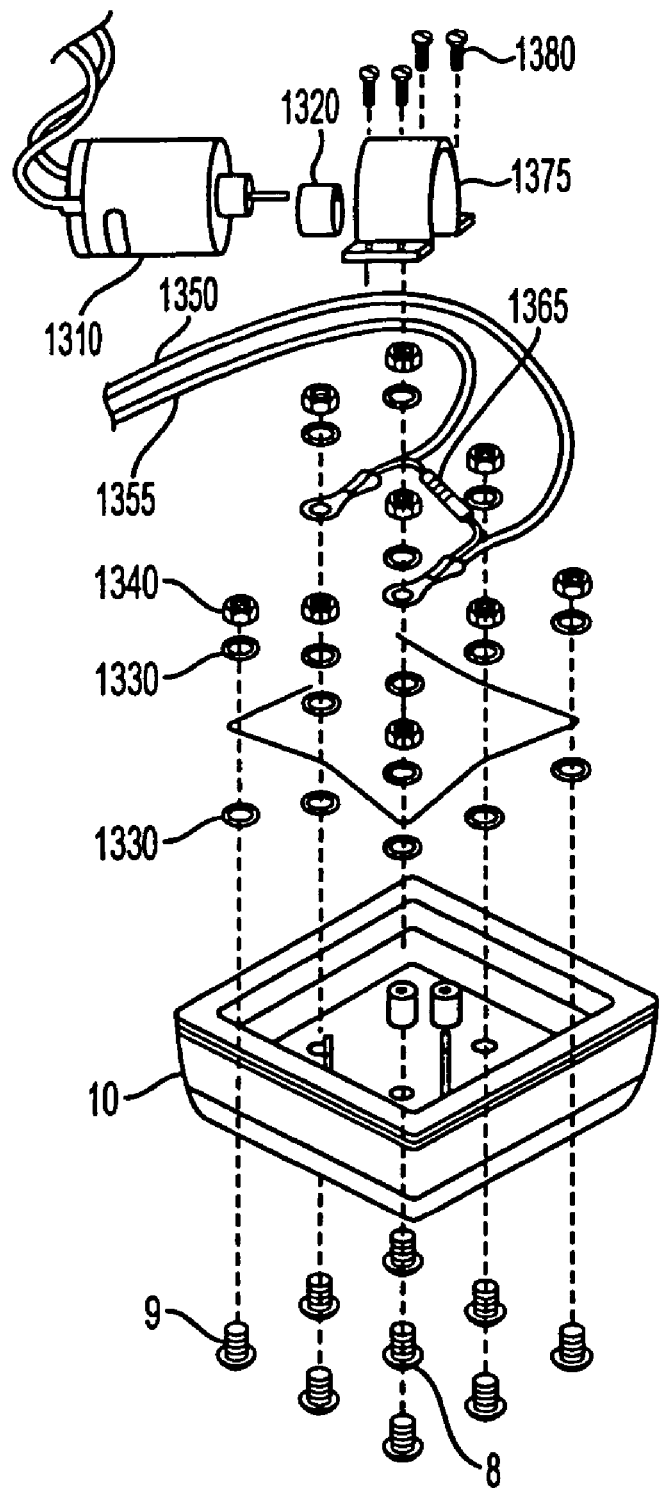
FIG. 13 shows components used to couple electrodes and wires to a head of the electroporation device according to the ninth embodiment of the invention.

FIG. 13 shows a back view of the head 10, whereby components used to couple the electrodes 8, 9 to the head and to provide an electrical connection to the electrodes 8, 9 are also shown in FIG. 13. A motor 1310, which includes an eccentric 1320 coupled to an output of the motor 1310, is used to provide mechanical vibrations to the head 10, so that the apparatus provides both electrical and mechanical vibrations to a patient's skin at the same time. These mechanical vibrations are preferable synchronized with the electrical pulses, as described earlier with respect to other-described embodiments of the invention.

The electrodes 8, 9 are preferably screwed onto the front plate of the head 10. Washers 1330 and screws 1340 are utilized to electrically couple wires 1350, 1355 to the electrodes 8, 9. In particular, wire 1350 (that has one end coupled to one of the two outputs of the pulse generator as shown in FIG. 4, for example) is electrically connected to the central electrode 9, and wire 1355 (that has one end coupled to the other of the two outputs of the pulse generator as shown in FIG. 4, for example) is electrically connected to the circumferential electrodes 8. Resistor 1365 is provided between the wires 1350, 1355, in the preferred construction. Also shown in FIG. 13 is a housing 1375 which is coupled to the head 10 by way of screws 1380. The eccentric 1320 moves within the housing 1375, thereby causing vibrations that are translated to the head 10 of the probe.

Figure 15:
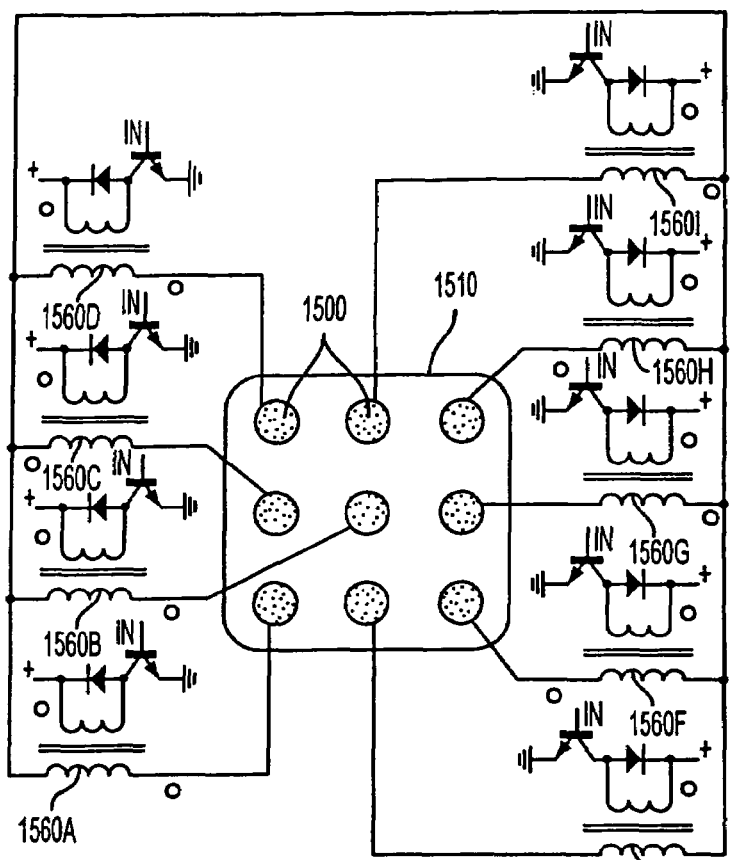
FIG. 15 shows a back view of the head of a probe, along with transformers shown, in an apparatus according to a tenth embodiment of the invention.
Figure 16:
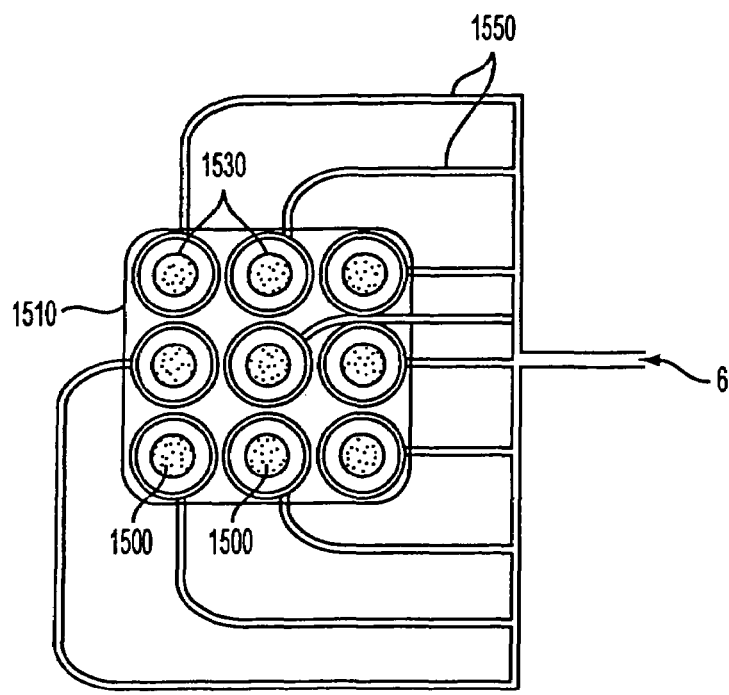
FIG. 16 shows a front view of the head of a probe used in an apparatus according to the tenth embodiment of the invention.

A tenth embodiment of the invention will be described herein with respect to FIGS. 15 and 16. The tenth embodiment is similar to the ninth embodiment, but utilizes a different configuration for the head, as well as providing a plurality of transformers (see FIGS. 4, 4A and 4B). FIG. 15 shows a back view of the electrodes 1500 disposed on a head 1510 of a probe, and FIG. 16 shows a front (skin-side) view of the electrodes 1500, whereby each electrode has a groove or trough 1530 surrounding it. Each groove 1530 has an outlet that extends to an edge of the head 1510, to thereby allow a respective tube 1550 to be fitted therein, so as to provide an amount of substance from the syringe 6 to the grooves 1530. That way, the tubes 1550 do not extend above the top surface of the head 1510. As an alternative to the multi-port tube configuration shown in FIG. 16, a number of syringes equal in number to the number of electrodes may be provided, with a tube provided to couple a syringe to an electrode.

In the tenth embodiment, each electrode 1500 is active and is connected to its own pulse transformer 1560A-1560I. The substance from the syringe 6 is provided to grooves 1530 surrounding each of the electrodes 1500. The electronic pulses are provided to each of the electrodes 1530 from the respective pulse transformers 1560A-1560, whereby transformers 1560C, 1560E, 1560G and 1560I provide positive pulses to their respective electrodes, and whereby transformers 1560A, 1560B, 1560D, 1560F and 1560H provide negative pulses to their respective electrodes at the same time, for the nine electrode configuration. More particularly, transformers 1560C, 1560E, 1560G and 1560I have their primary and secondary windings connected in phase, and transformers 1560A, 1560B, 1560D, 1560F and 1560H have their primary and secondary windings connected 180 degrees out of phase (see oppositely-positioned dots for those transformers in FIG. 15). If a square wave is applied to all of the primary windings of the transformers at the same time and when there is a positive transition from low to high, the transformers with their primary and secondary windings in phase with each other will output a positive exponential pulse, and the transformers with their primary and secondary windings 180 degrees out of phase with each other will output a negative exponential pulse.

In the tenth embodiment, it is preferable that a first group of electrodes receive a positive pulse at a same time a second group of electrodes (equal or nearly equal in number to the first group, preferably) receive a negative pulse, to provide a good skin transpiration effect. The type of pulses, the burst duration, the frequency, etc., are similar to the embodiments described earlier. Also, the tenth embodiment may include a mechanical vibration that is applied to the patient's skin at the same time the electrical pulses are applied to the patient's skin, in a manner described previously.

In an eleventh embodiment, a plurality of transformers are respectively provided to output electrical pulses to a plurality of electrodes disposed on a head portion of a probe, whereby the plurality of transformers provide separate and independent pulse bursts to their respective electrodes. For example, each of the pulse generators in the eleventh embodiment may have different phase shift amounts within a range of from 0 degrees to 360 degrees. In this regard, the output pulses from the transformers are synchronized with each other, to have a particular out-of-phase relationship with respect to each other.

Figure 17:
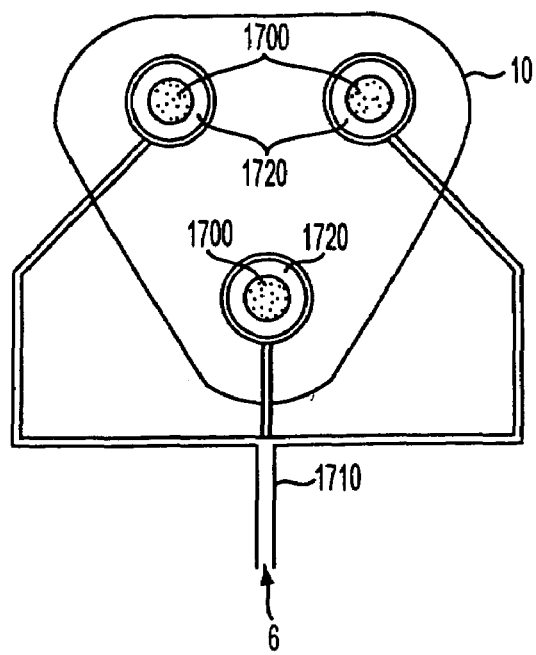
FIG. 17 shows a front view of the head of a probe having three electrodes, which is used in an apparatus according to an eleventh embodiment of the invention.
Figure 18:
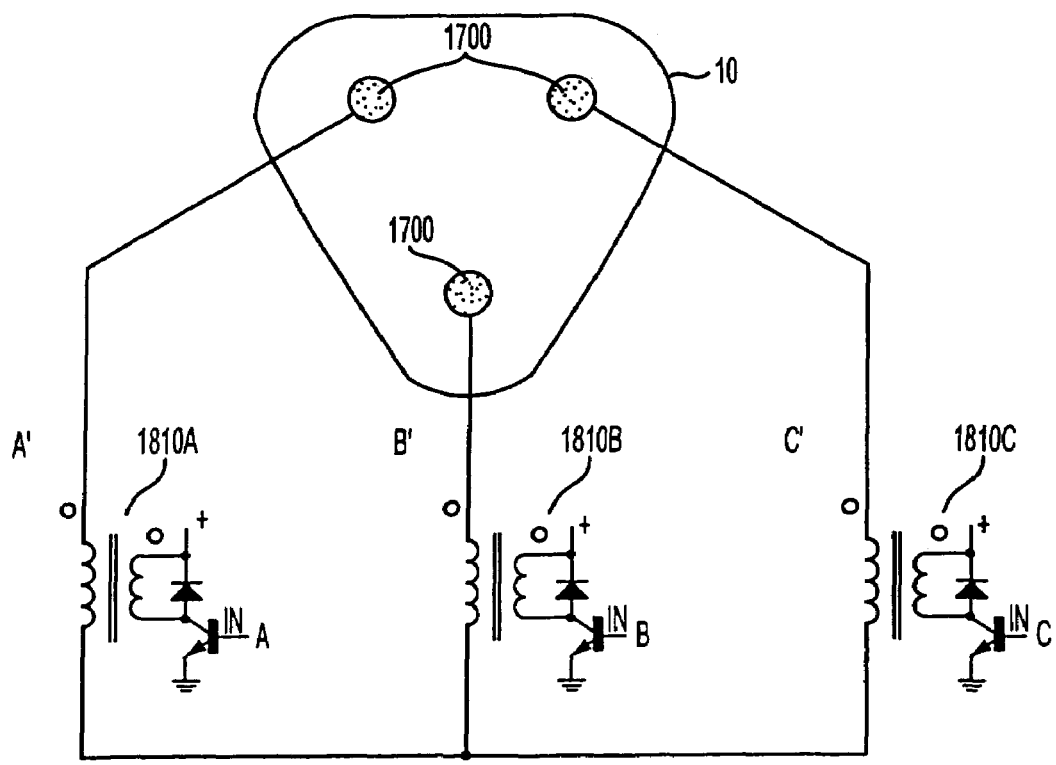
FIG. 18 shows a back view of the head of a probe having three electrodes, along with transformers providing electronic pulses to the three electrodes, which is used in an apparatus according to the eleventh embodiment of the invention.
Figure 19:
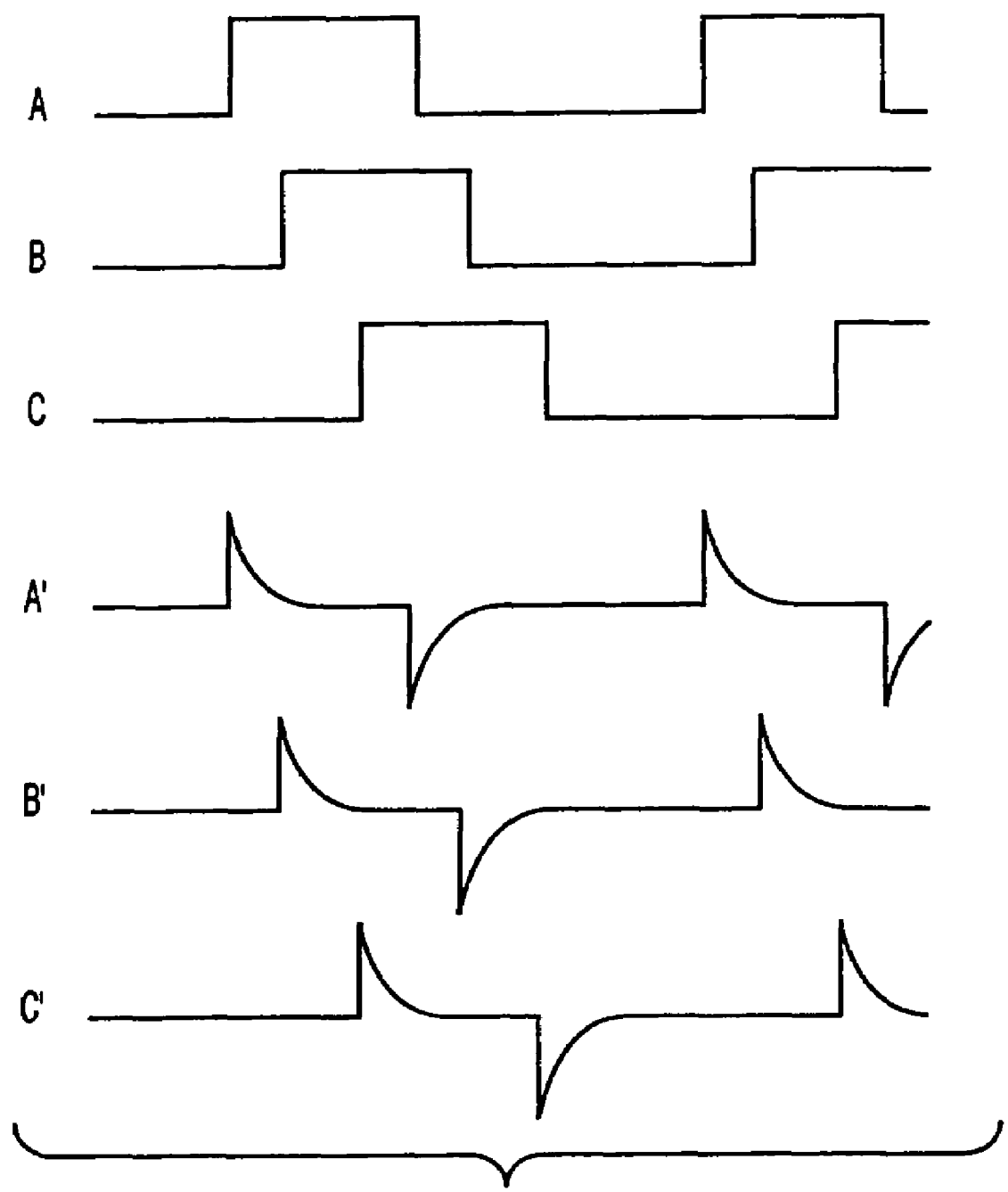
FIG. 19 shows staggered square-wave input pulses and exponential outputs pulses with respect to the three transformers which is used in an apparatus according to the eleventh embodiment of the invention.

One example of an electrode array according to the eleventh embodiment is shown in FIGS. 17, 18 and 19. This example provides a three electrode configuration, with no central electrode. Referring now to FIG. 17, which shows a front side of the head 10, electrodes 1700 are respectively coupled via tube 1710 to a syringe 6, to receive a substance in a groove 1720 surrounding each of the electrodes 1700. Like the previously-described embodiments, as shown in FIG. 14, a groove or path to an end of the head 10 is provided, in order to fit the tube 1710 snugly within it so that the tube 1710 does not extend above the upper surface (plate) of the head 10 that makes contact with a patient's skin.

Referring now to FIG. 18, which shows a back side of the head 10, transformers 1810A, 1810B and 1810C respective provide pulses of the same polarity, but delayed from each other by a particular amount, to the corresponding one of the electrodes 1700 coupled to each transformer. FIG. 19 shows the input square wave pulses that are provided to each transformer, whereby the square wave pulses that are input to transformer 1810C are delayed a certain amount (e.g., 30 degrees) with respect to the square pulses that are input to transformer 1810B, which in turn are delayed a certain amount (e.g., 30 degrees) with respect to the square wave pulses that are input to transformer 1810A. This can readily be done by providing the trigger "IN" signal to each of the respective transformers 1810A, 1810B, 1810C at the appropriate timings. The result are exponential pulses that are output from each of the three pulse generators, whereby the exponential pulses are phase-shifted a fixed amount with respect to each other.

With the three-electrode and three-pulse-generator configuration as shown in FIGS. 17-19, it is possible to provide a 120 degree phase shift with respect to the signals output by the three pulse generators (e.g., one signal output at 0 degrees, one signal output at 120 degrees, and one signal output at 240 degrees). This provides a rotation of the electric field between the electrodes 1700 in a manner similar to what happens with a rotation of a three-phase motor. More generally, in the eleventh embodiment, using a number "n" of electrodes and "n" pulse generators, one of ordinary skill in the art will understand that one can devise any particular type of electric field distribution on the skin surface to be treated by way of an apparatus according to the eleventh embodiment, as desired.

Figure 20:
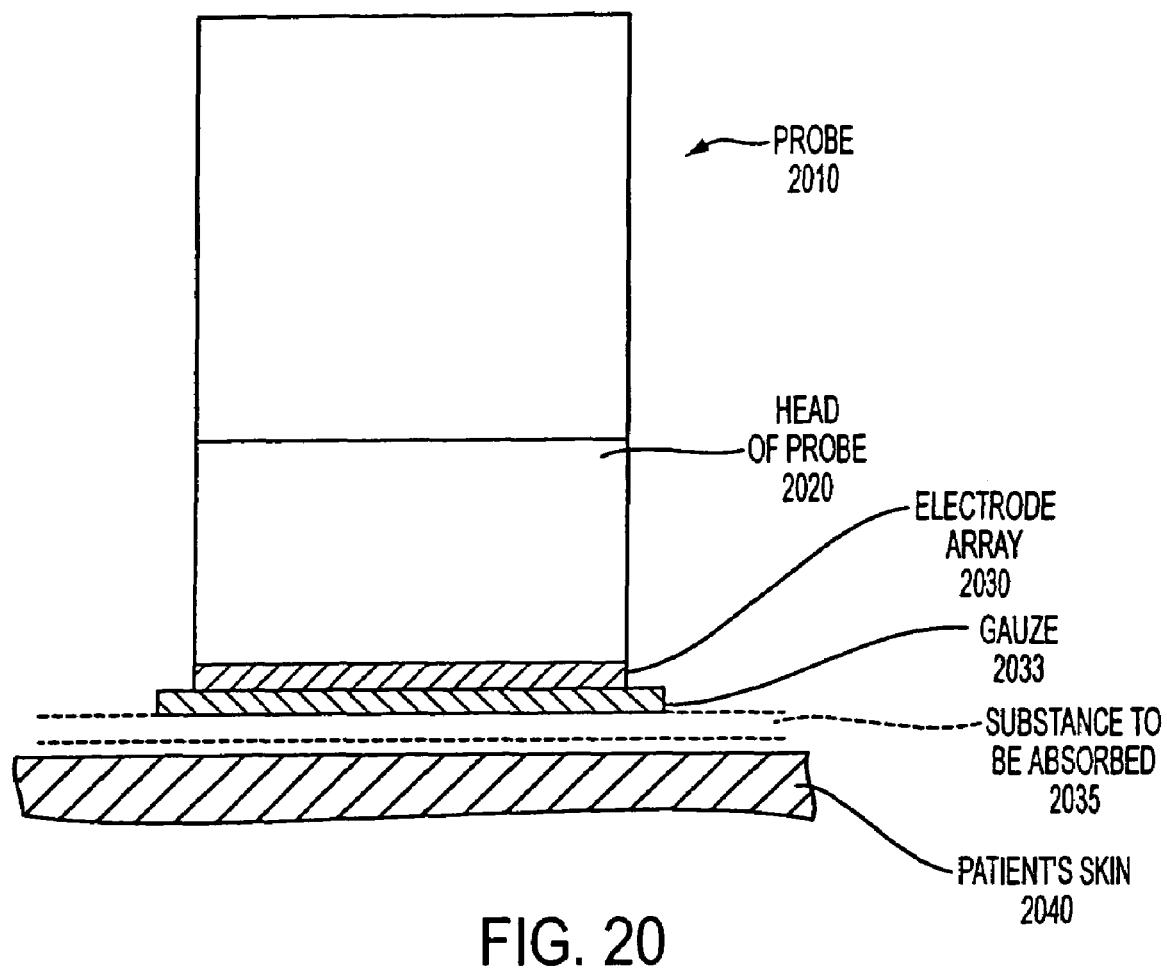
FIG. 20 shows a gauze pad provided between a probe (according to any of the embodiments of the invention) and a patient's skin, according to a twelfth embodiment of the invention.
Figure 21:
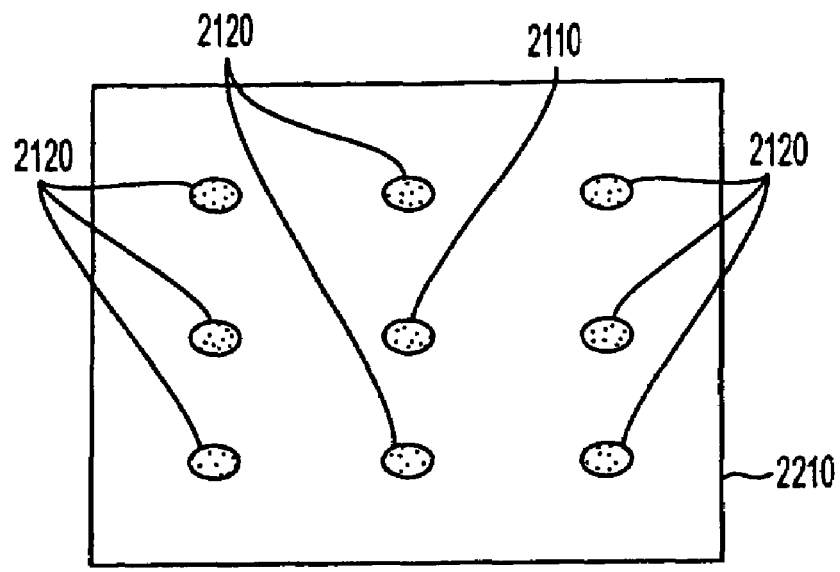
FIGS. 21-24 show different views of a skin treatment device according to a thirteenth embodiment of the invention.
Figure 22:
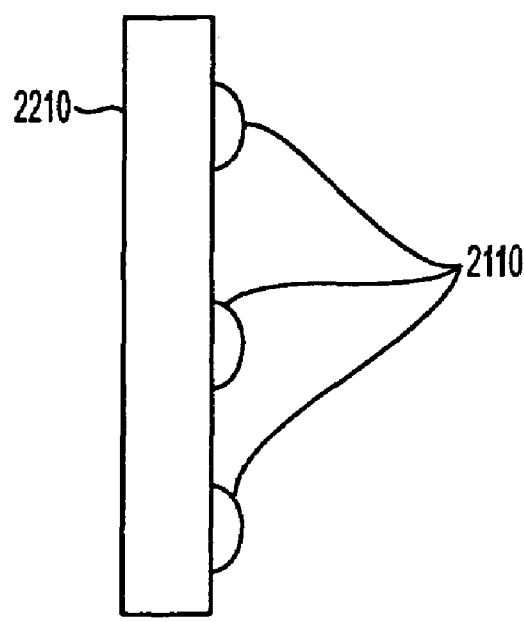
Figure 23:
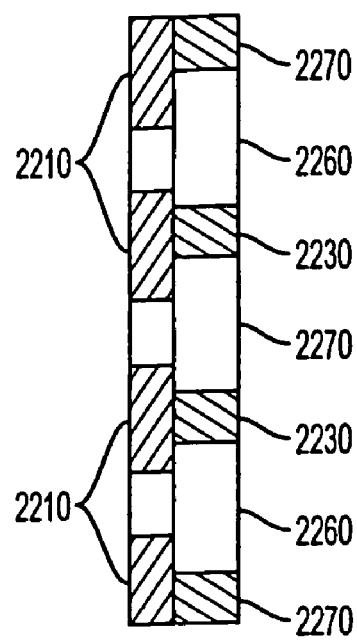
Figure 24:
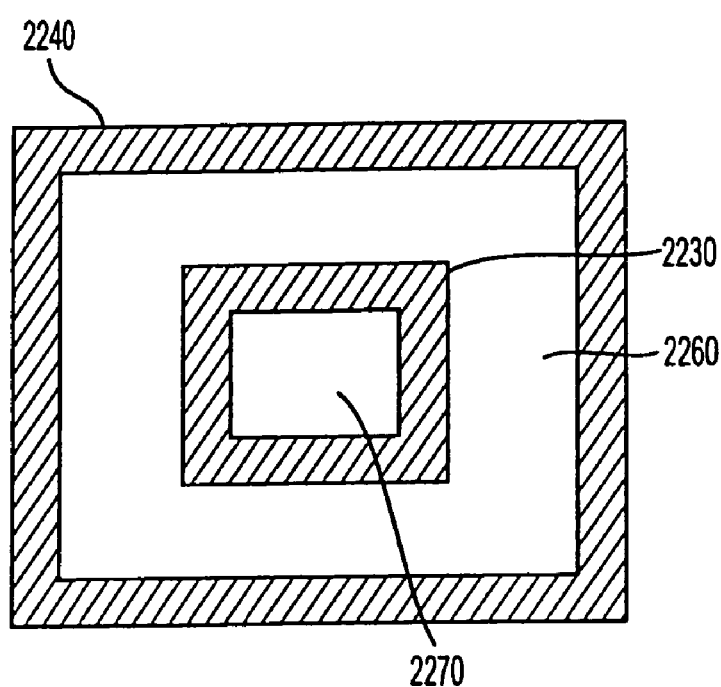

A twelfth embodiment of the invention will be described below with reference to FIG. 20. In the twelfth embodiment, a probe 2010 is used to provide a skin-absorbing substance to the skin. In that regard, the probe 2010 may be a probe according to any of the previous embodiments of the invention described earlier in this application. As shown in FIG. 20, the probe 2010 has a vibrating head 2020 and an electrode array 2030 provided at an end portion of the vibrating head 2020. In the twelfth embodiment, gauze 2033 is provided between the head 2020 of the probe 2010 and the patient's skin 2040. Preferably, the gauze 2033 is a pad having a same size (or substantially the same size) as the head 2020 of the probe 2010 or larger in order to cover the treatment area where the head 2020 is supposed to be moved. In a preferred implementation, the gauze 2033 is a pad (e.g., rectangular or square shaped, with a thickness between 0.1 to 1 mm) that is commercially available on the market. With the gauze 2033 provided between the probe 2010 and the patient's skin 2040, the probe 2010 does not come into direct contact with the patient's skin 2040. The gauze 2033 allows for the probe 2010 to be moved over the patient's skin 2040 in an easier manner and with less friction than in a case where the gauze 2033 is not utilized. Also, the inventor has found out that the use of the gauze 2033 provides for a more even application of the skin-absorbing substance 2035 to the patient's skin 2040. As an alternative to gauze, other types of pads, such as a cotton tissue or a synthetic (e.g., nylon) tissue, may be used between the patient's skin 2040 and the probe 2010. All of these pads have a characteristic of sufficient porosity to allow the skin-absorbing substance 2035 to pass from (its container within) the head 2020 of the probe 2010 (for those embodiments in which the skin-absorbing substance 2035 is stored within the head 2020 of the probe 2010) and through the pad 2033 and thereby onto the patient's skin 2040.

In the present invention according to the twelfth embodiment, an important feature is that gauze is provided between the head of the probe and the patient's skin. In one possible implementation, the gauze is affixed to the head of the probe and not to the patient's skin. In another possible implementation, the gauze is affixed to the patient's skin and not to the head of the probe. With either implementation, one obtains a more even distribution of the skin absorbing substance to the skin (as compared to the case whereby no gauze is utilized), and at the same time allows the head of the probe to be moved across the patient's skin (to treat a particular region of the patient's skin) with less friction (as compared to the case whereby no gauze is utilized). The gauze can be releasably affixed to the patient's skin in one possible implementation of the twelfth embodiment in a variety of ways, such as by using medical tape. The gauze can be releasably affixed to the head of the probe in another possible implementation of the twelfth embodiment in a variety of ways, such as by rubber-banding the gauze pad to the head of the probe (with the rubber band gripped around the sidewalls of the head of the probe), or by using adhesive tape to adhere the peripheral edges of the gauze pad to the sidewalls of the head of the probe, or by providing a gauze pad with an outer (e.g., plastic) sheath that allows the gauze pad to be easily fitted onto and off of the head of the probe. In any of these cases, the gauze can be readily removed from the patient's skin or the head of the probe, and disposed after use.

In a thirteenth embodiment of the invention, with reference to FIGS. 21-24, a skin treatment device is configured to deliver a defined amount of lidocaine, ascorbic acid, or other type of skin treatment drug into the dermis. On the head of a probe which can be constructed as described with respect to the third embodiment, i.e., with a central electrode 2110 and eight electrodes 2120 disposed around the central electrode, where the central electrode 2110 is connected to one output of the pulse transformer and the eight electrodes 2120 are connected to the other output of the pulse transformer, a plate 2210 is coupled to the head (see FIGS. 23 and 24), with the electrodes 2110, 2120 provided between the head 2130 of the probe and the patient's skin.

The plate 2210 is preferably a plastic layer (with a thickness of 300 microns in a preferred implementation), where there are drilled nine holes that correspond to the nine electrodes disposed on the head. The plate preferably has a top surface area of 60 mm×60 mm (on which the electrodes are disposed at different points on the top surface area). On top of the plastic layer 2210 are glued (other methods of adhering may be contemplated while remaining within the scope of the invention, such as taping) two concentric squares 2230, 2240 made of non conductive rubber. Each of the concentric squares 2230, 2240 preferably has a 5 mm width and a 5 mm thickness. Between the outer square 2240 and the inner square 2230, a first (or outer) gauze pad 2260 is fitted. A second (or inner) gauze pad 2270 is fitted within the inside of the inner square 2230. The outer gauze pad 2260 is thereby in contact with the eight electrodes 2120, while the inner gauze pad 2270 is in contact with the central electrode 2110. The inner square 2230 provides an electrical separation between the inner gauze pad 2270 and the outer gauze pad 2260, and the outer square 2240 operates to hold the outer gauze pad 2270 in place against the top surface of the plate 2210. The inner gauze pad 2270 and the outer gauze pad 2260 preferably have the same thickness, 5 mm, as the thickness of the inner square 2230 and the outer square 2240.

In a preferred implementation of the thirteenth embodiment, the outer gauze pad 2240 is soaked with around 2 ml. of fisiological solution (1% NaCI) and the inner gauze pad is soaked with 0.5 ml. of 5% lidocaine cloridrate water solution. The plate 2210 is disposed between the patient's skin and the vibrating head of the probe.

An experiment performed on a mouse demonstrated that the same amount of radioactive lidocaine is transported in to the skin, after a microdermabrasion treatment, by the system and method according to the thirteenth embodiment, as compared to an iontophoretic device set at the same value of the product of the current * ("*" is a multiplication operator) time, where the current of the iontophoretic device is set in order to be in a first positive phase positive and in a second negative phase and the current of the system and method according to the thirteenth embodiment is set such that the product average current per pulse per total time of the positive pulses has the same value as the positive phase of the iontophoretic device, and the product average current per pulse per total time of the negative pulses has the same value as the negative phase of the iontophoretic device.

The experiment described above demonstrated the advantages of the present invention according to the thirteenth embodiment as compared to the use of an iontophoretic device. One advantage of the present invention, thanks in part to the use of symmetrical pulsed current, is that it does not cause a chemical reaction at the electrodes. An iontophoretic device, on the other hand, causes electrolysis with change of PH on the skin and thereby can result in an adverse effect on the skin (e.g., redness on the skin, inflammation on the skin, burns on the skin). The use of the present invention according to the thirteenth embodiment allows one to provide skin absorption treatment to the skin after a microdermabrasion has been performed on the skin which removed the stratum corneum (the outer layer of the skin that is exposed to air), whereby the use of an iontophoretic device to provide skin treatment could cause higher damage if a change of PH on the skin occurs. This problem does not occur when the thirteenth embodiment of the invention is utilized instead of an iontophoretic device. The use of the two techniques together (dermabrasion and then skin treatment by utilizing the system or method according to the thirteenth embodiment) gives a higher flow of a skin treatment substance (about 50% increase) as demonstrated by the experiment on the mouse.

A further advantage of the present invention according to the thirteenth embodiment as compared to an iontophoretic device is that the present invention according to the thirteenth embodiment allows for the possibility to use any type of ionic water-based substance as a skin treatment substance without the risk of chemical reaction at the electrodes that could change the characteristics of the applied substance and thereby cause an adverse effect on the skin. The causing of an adverse effect on the skin is a situation that could occur in an iontophoresis treatment and thereby prevents the use of many substances to be applied to the skin. This problem does not occur when the system or method according to the thirteenth embodiment is utilized instead.

In an alternative implementation of the thirteenth embodiment, the two gauze pads are substituted with two hydrogel pads, the outer pad with 1% NaCI and the inner pad with 5% Lidocaine Cloridrate. Besides NaCI, other types of solutions for the outer pad may include other water-based ionic conductive substances, or the same substance as used in the inner pad, for a larger absorption surface. Besides lidocaine cloridate, other types of solutions for the inner pad may include: ascorbic acid, jaluronic acid, collagen, elastin, cogic acid, salicilic acid, liposomes, anti-inflammatory steroids or local anesthetics.

In the case of this embodiment, the use of synchronous mechanical vibrations together with a burst of pulses give a small increase of absorption rate, and it also gives a decrease in the sensitivity of the patient to the pain generated by the current pulse, thereby enabling the increase of the pulse current that is acceptable by the patient (that is, a pulse current level that does not cause any physical discomfort to the patient).

While the thirteenth embodiment has been described with respect to an electrode configuration such as shown in the third embodiment described previously, it may also be utilized with other types of electrode configurations, whereby a first set of electrodes are covered by a first solution-absorbing pad such as the ones described above, and whereby a second set of electrodes not electrically connected to the first set of electrodes) are covered by a second solution-absorbing pad such as the ones described above.

Experimental results of the application of the several embodiments of the skin absorption apparatus described hereinabove to the skin demonstrated that a noticeable variation of results and rate of absorption of substances occurred. The analysis was carried out over an area of skin previously dermabraded with a standard microdermabrader available on the market and an adjacent area not previously dermabraded. This analysis demonstrated that the results obtained in the dermabraded area are fairly constant and reproducible while the results in the non-dermabraded area are variable and somewhat inconsistent. This inconsistency is due to the fact that the stratum corneum (also referred to as the horny or dead outermost layer of the epidermis) of the skin acts like a barrier to the absorption of the substances applied to the skin, and moreover it increases the electrical resistance of the skin, thereby somewhat decreasing the absorption effect of the skin absorption treatment according to the invention.

The thickness of the stratum corneum is variable from person to person, and moreover it is variable from time to time in the same person. This induces a variability that makes it difficult to come up with a standard application time of the skin absorption apparatus according to the various embodiments of the invention. For this reason, according to yet another embodiment of the invention, a skin absorption treatment method includes a microdermabrasion performed before the application of the skin absorption apparatus in order to give more reproducible and more constant results as compared to the embodiments in which a microdermabrasion is not first performed. The microdermabrasion to be performed prior to the skin absorption treatment may be one described in various U.S. patents assigned to Mattioli Engineering, Ltd., such as U.S. Pat. Nos. 6,322,568 and 6,039,745, each of which are incorporated in their entirety herein by reference, or other types of dermabrasion treatments conventionally known.

Preferably, the dermabrasion treatment is performed for three minutes in order to remove a 100 micron layer of the stratum corneum layer of the skin in an area to be later treated with a skin absorption enhancement device according to one of the embodiments of the invention. Ideally, the skin absorption treatment is performed soon after (e.g., within 5 minutes) of the completion of the dermabrasion treatment. Of course, other time lengths of dermabrasion treatment, depth of stratum corneum removal, and time between the dermabrasion treatment and the skin absorption treatment, may be contemplated while remaining within the scope of the invention as described hereinabove.

A fourteenth embodiment of the invention will now be described in detail. The fourteenth embodiment of the invention is directed to a method and apparatus for skin absorption enhancement and cellulite reduction, and it can be used as a modification of the fifth or eighth embodiments described previously. In the fourteenth embodiment, in order to increase the speed and efficiency of the cellulite reduction, it has been determined by the inventor that a controlled heating of the skin surface and the area beneath the skin surface having the cellulite and the fatty tissue, causes an increase in the absorption rate of a substance to be introduced into the skin (and thereby to the region beneath the skin having the cellulite and the fatty tissue). This results in a faster and more efficient reduction of cellulite and fatty tissue in the patient.

The heating of the skin may be effected in at least two different ways: a) a 50 W infrared heating lamp positioned between rollers positioned on the head of the probe, or b) a radio frequency at a frequency of 13.54 MHz, 50 W power, whereby the rf is provided to the skin by way of the rollers positioned on the head of the probe.

With respect to the controlled heating of the skin, by way of example and not by way of limitation, the skin surface is preferably heated to a temperature of 50 degrees C, at a rate of 5 degrees C per second. More generally, the skin may be heated to a temperature of between 45 degrees C and 60 degrees C, at a rate of between 2 degrees C per second and 40 degrees C per second.

If heating is to be effected by way of a radio frequency, the radio frequency is preferably a continuous wave (CW), but it may alternatively be a wave having a particular duty cycle (e.g., between 20% and 80%). In an alternative configuration, a temperature sensor is provided on the head of the probe, to determine when the skin reaches the desired temperature. When the desired skin temperature is reached, the heating of the skin is controlled so that the desired skin temperature is maintained (and thus not increased). Thus, when the patient's skin is detected to be at 50 degrees C, then the radio frequency is controlled so that it is changed from a CW signal to a pulsed signal, so that the heat applied to the skin is lessened so as to maintain the desired skin temperature during the skin treatment.

Besides using a 50 W infrared heating lamp, an LED (light emitting diode) or laser diode may be used instead, and also an optical light range (e.g., 300 μm to 10 82 m) may be used instead of the infrared range. Furthermore, the power output of the lamp need not necessary be 50 W (e.g., it can be in a range of from 25 W to 100 W).

Besides using a 13.54 MHz, 50 W radio frequency signal, a radio frequency of between 0.5 MHz and 27 MHz may be used instead, and a power output may be anywhere between 1 to 100 W. A lower radio frequency results in the heating of a deeper portion beneath the skin surface, and a higher radio frequency results in the heating of a shallower portion beneath the skin surface. Thus, the particular radio frequency to use may be dependent on the area within the patient to be treated.

Figure 25:
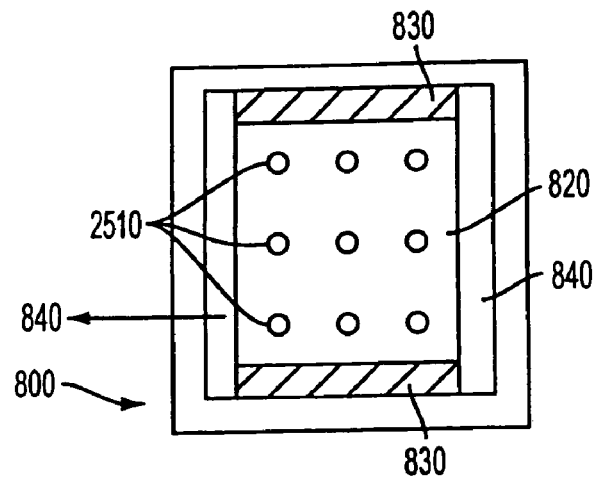
FIGS. 25-27 show one possible implementation of a skin treatment device according to a fourteenth embodiment of the invention.
Figure 26:
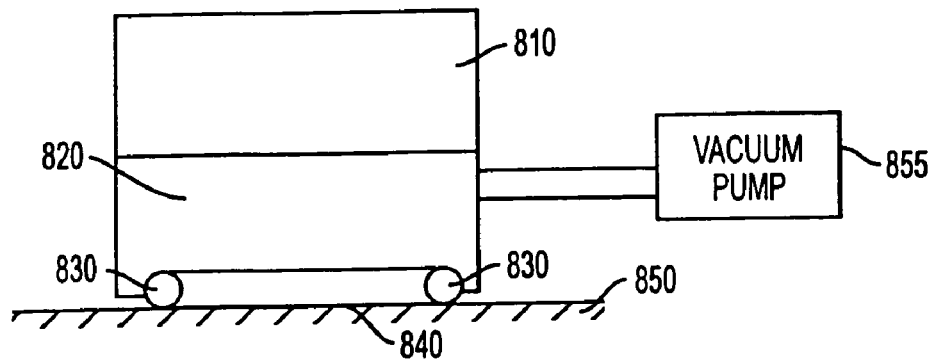
Figure 27:
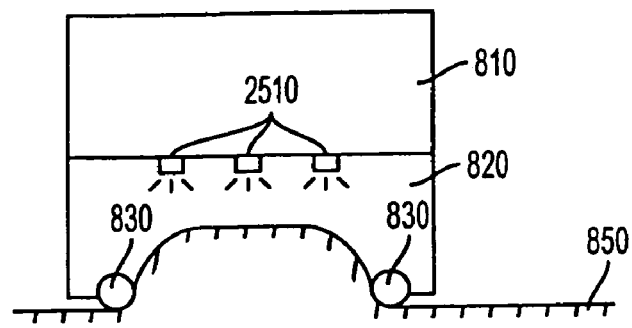

Referring now to FIGS. 25, 26 and 27, one possible implementation of the fourteenth embodiment is shown. Infrared light emitting diodes (LEDs) 2510 are provided on a head of a probe, whereby the LEDs 2510 are positioned on a skin-facing surface of the vibrating plate 810. When the skin is sucked into the probe head by way of the vacuum chamber 820 and the vacuum pump 855, the skin 850 is heated by way of the LEDs 2510, thereby causing a heating (solubilizing) of the cellulite/fat tissue beneath the skin surface. When a substance is applied to the skin by way of the probe, that substance can readily attach to the heated cellulite/fat tissue, whereby the cellulite/fat tissue can be more easily metabolized by the patient, to thereby lose the cellulite and fat. Also shown in FIGS. 25, 26 and 27 is a rubber belt 840 that is coupled around the rollers 830.

Figure 28:
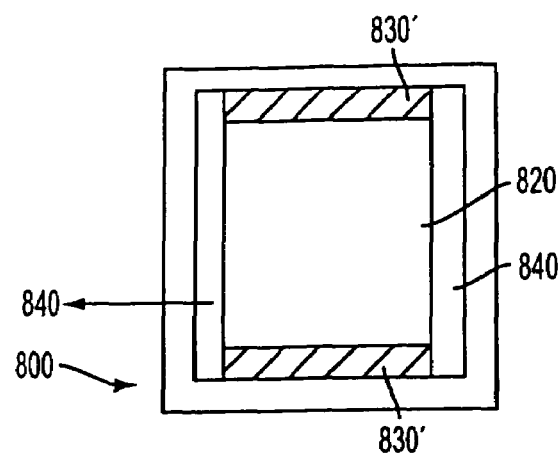
FIGS. 28-31 show another possible implementation of a skin treatment device according to the fourteenth embodiment of the invention.
Figure 29:
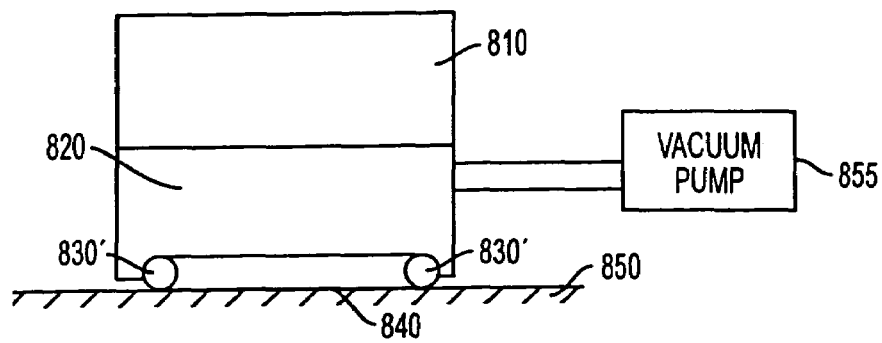
Figure 30:
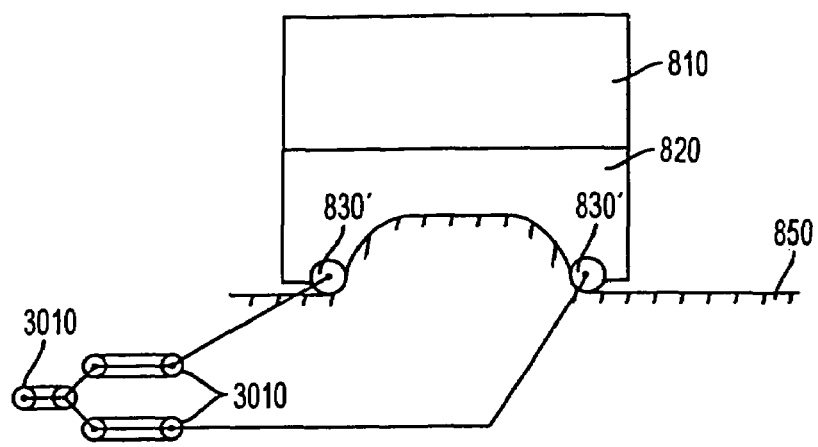
Figure 31:
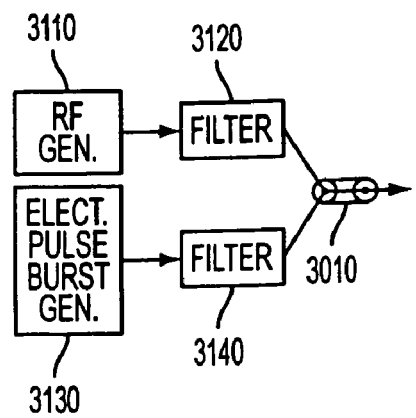

Referring now to FIGS. 28, 29, 30 and 31, another possible implementation of the fourteenth embodiment is shown. In FIGS. 28, 29 and 30, the rollers are conductive rollers 830' that provide the means for the electrical pulse bursts to be applied to the patient's skin. Also, the conductive rollers 830' provide the mechanism for the heating radio frequency signal to be directly applied to the patient's skin. The rollers 830' are preferably metal rollers or conductive plastic rollers. Also shown in FIG. 30 are coaxial cables 3010 that provide the path for the electrical pulse bursts and the heating radio frequency signal to be provided to the rollers 830' disposed on the head of the probe. FIG. 31 shows one possible way in which these signals can be provided to the rollers 830', whereby a radio frequency generator 3110 outputs a radio frequency signal, which then passes through a first filter 3120, and then on to the coaxial line 3010. A electrical signal burst generator 3130 outputs bursts of electrical pulses, which then pass through a second filter 3140, and then on to the coaxial line 3010. The first filter 3120 has a bandwidth such that it blocks the electrical pulse bursts from entering the radio frequency generator 3110, and the second filter 3150 has a bandwidth such that it blocks the heating radio frequency signal from entering the electrical signal burst generator 3140. One possible circuit implementation of the electrical signal burst generator 3140 is shown in FIG. 4, for example.

As described with respect to an earlier embodiment, a preferred frequency of each of the electrical pulses in the bursts of electrical pulses is between 2500 and 3000 Hz, and thus the first filter 3120 may be configured to block out this particular frequency range (but to pass through frequencies greater than 1 MHz). Similarly, the second filter 3150 may be configured to block out frequency ranges greater than 1 MHz while allowing lower frequency signals to pass therethrough (e.g., it is a low-pass filter).

A fifteenth embodiment of the invention will be described below, with reference to FIGS. 32A-C, 33A, 33B, and 33A-C. The fifteenth embodiment provides an alternative way of providing a substance to the skin of a patient by way of a component coupled to a head of a probe that provides electrical pulses and/or mechanical vibrations to the patient's skin. In that regard, the fifteenth embodiment is similar to the thirteenth embodiment described previously, but whereby the way that a skin-treating substance is applied to the skin is done in a different manner.

Figure 32A:
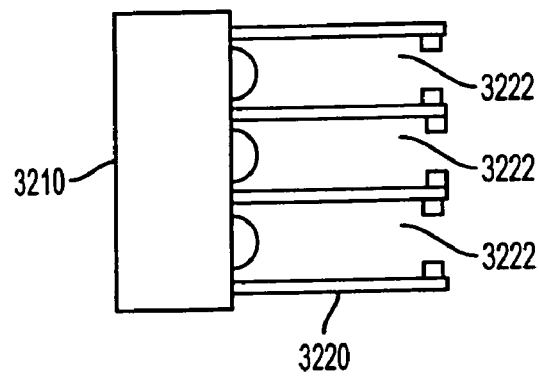
FIGS. 32A, 32B and 32C show one possible implementation of a skin treatment device according to a fifteenth embodiment of the invention.
Figure 32B:
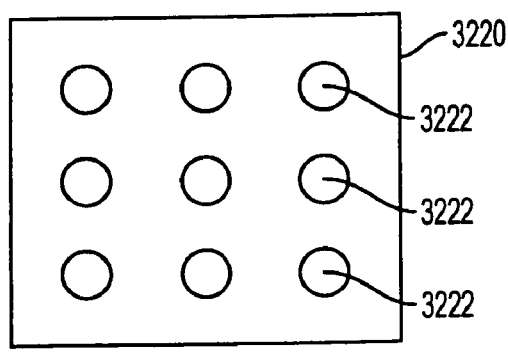
Figure 32C:
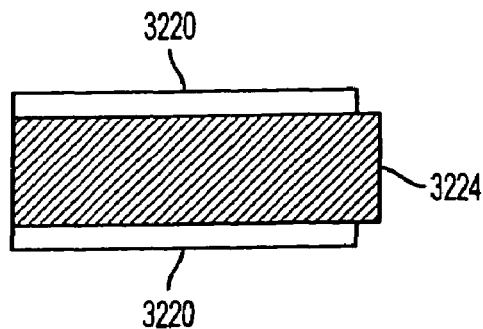

FIG. 32A shows a side sectional view of a probe head 3210 that is coupled to a head attachment 3220. The head attachment 3220 is preferably made from polypropelene (it can be a plastic component), and it has nine cylindrical openings 3222 that allow nine separate cylindrical sponges to be fitted therein. FIG. 32B shows a front view of the head attachment 3220, and FIG. 32C shows a side sectional view of one of the cylindrical openings 3222 of the attachment head 3220, whereby a cylindrical sponge 3224 is fitted within the cylindrical opening 3222. Alternatively to using cylindrical sponges, cotton gauzes or hydogel pads can be fitted within the cylindrical openings 3222, or a combination of these components may be used (e.g., three gauze pads, three sponges, and three hydrogel pads). The attachment head 3220 is shown having nine separate cylindrical openings 3220 for the case where there are nine electrodes disposed on the face of the probe, whereby FIG. 32A shows three of the electrodes 3230 in a side view (the other electrodes on the face of the probe are blocked from view, but see FIG. 2C for the disposition of the nine electrodes).

Each of the nine electrodes on the face of the probe is disposed at one end of the cylindrical opening 3222, whereby the sponge 3224 extends slightly out from the other end of the cylindrical opening 3222, as seen best in FIG. 32B. That way, the sponge is made to be in contact with an area of the patient's skin to be treated by way of the probe. Each sponge 3222 is soaked with a substance to be applied to the patient's skin, whereby one may have hydrogel pads soaked with 4% lidocaine, for example. With the electrical pulses being applied to the patient's skin by way of the electrical pulses (that are indirectly connected to the patient's skin by way of the sponges 3222) and/or by the mechanical vibrations, the substance provided on the sponges 3222 is readily absorbed within the patient's skin.

In a preferred configuration, the attachment head 3220 is a disposable component, that can be thrown away when after a patient has been treated. The attachment head 3220 may be detachably coupled to the probe head 3210 in any of a variety of ways, such as by using a snap-on coupling, or by other ways that have been described previously with respect to other embodiments. Of course, if the disposition and number of electrodes is different on the probe head 3210, the disposition and number of openings on the attachment 3220 will change to accommodate that particular disposition.

Figure 33A:
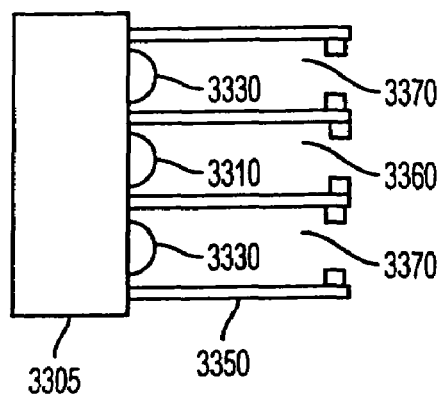
FIGS. 33A and 33B show another possible implementation of a skin treatment device according to the fifteenth embodiment of the invention.
Figure 33B:
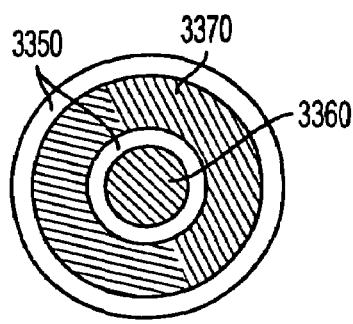

FIGS. 33A and 33B show a second type of electrode disposition, in which a central electrode 3310 is provided beneath a centrally-positioned sponge 3320, and in which peripheral electrodes 3330 are provided beneath a peripherally-positioned sponge 3340. In this configuration, the probe head 3305 has a circular shape, whereby the attachment head 3350 has an inner cylindrical opening 3360 for accommodating the centrally-positioned sponge 3320, and an outer cylindrical opening 3370 for accommodating the peripherally-positioned sponge 3340. FIG. 33A shows a side sectional view of the probe head 3305 with the attachment head 3350 coupled thereto, and FIG. 33B shows a front view of the attachment head 3350 with the sponges fitted within the respective openings of the attachment head 3350.

Figure 34A:
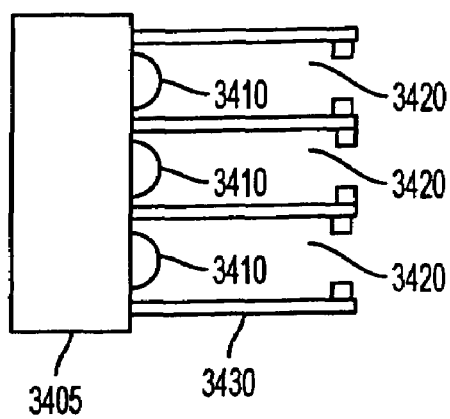
FIGS. 34A, 34B and 34C show still another possible implementation of a skin treatment device according to the fifteenth embodiment of the invention.
Figure 34B:
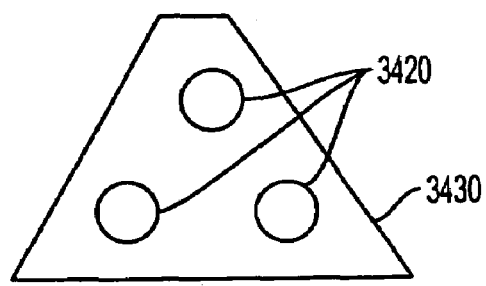
Figure 34C:
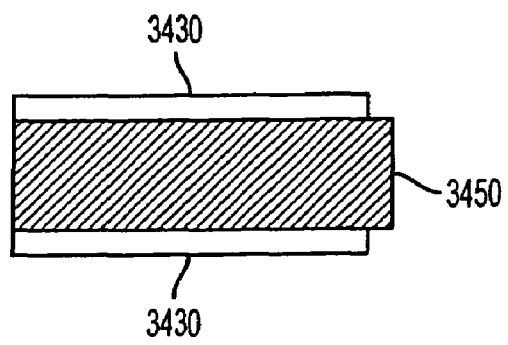

FIGS. 34A-34C show a third type of electrode disposition on a probe head 3405. This disposition corresponds to the one shown in FIGS. 17 and 18 of the drawings, for example, whereby there is not any centrally-positioned electrode on the probe head 3405. In this configuration, the three electrodes 3410 are provided beneath the respective three cylindrical openings 3420 of the attachment head 3430, whereby the attachment head 3430 may be made out of polypropelene, for example. Each of the cylindrical openings 3420 may be filled with a sponge or gauze that has been soaked with a substance to the applied to the patient's skin. FIG. 34A shows a sectional side view of the probe head 3405 with the attachment head 3430 detachably attached thereto, FIG. 34B shows a front view of the attachment head 3430 (without any sponges provided in the openings 3420), and FIG. 34C shows a side sectional view of one cylindrical opening 3420 with a sponge 3450 fitted therein.

Different embodiments of the present invention have been described according to the present invention. Many modifications and variations may be made to the techniques and structures described and illustrated herein without departing from the spirit and scope of the invention. Accordingly, it should be understood that the apparatuses described herein are illustrative only and are not limiting upon the scope of the invention. For example, the frequency of the mechanical vibration and the frequency of the bursts of electronic pulses may be the same, as described above with respect to several different embodiments, or they may be an integer multiple or submultiple of each other. For example, an electronic pulse burst frequency of 50 Hz may be utilized together with a mechanical vibration of 100 Hz, and still one would achieve an effect of increased absorption and decrease in skin sensitivity (e.g., lowering of the pain) to the patient. Alternatively, an electronic burst frequency of 200 Hz may be utilized together with a mechanical vibration of 100 Hz, and still one would achieve an effect of increased absorption and decrease in skin sensitivity. Also, the plate on which the electrodes are disposed on the probe may be a sterilized disposable part (e.g., removed from a sterilized container and then affixed to the head of the probe). In this implementation, when one is finished treating a patient, the disposable plate is removed from the probe and discarded, and then a new sterilized plate is affixed to the probe (with the electrodes provided thereon) in order to treat another patient. By such an implementation, this greatly reduces the possibility of contamination between different patients, since the portion of the probe directly in contact with each patient is discarded after treatment of each patient.

What is claimed is:

1. A treatment method for providing a substance to be absorbed onto a surface of a patient's skin, comprising:
    heating the surface of the patient's skin by one of: i) a radio frequency signal, and ii) a lamp, and
    applying the substance onto the surface of the patient's skin by way of a probe head that provides, at the same time: i) bursts of electrical pulses to the skin surface, and ii) vibrations to the skin surface,
    wherein the vibrations are applied to the skin surface at substantially a same frequency rate, a first harmonic of the same frequency rate, and/or a second harmonic of the same frequency rate, as a burst rate of electrical pulses being applied to the skin surface, and
    wherein the treatment method is for reducing cellulite or fatty tissue disposed beneath the surface of the patient's skin.

2. The treatment method according to claim 1, wherein the applying of the bursts of electrical pulses comprises:
    obtaining exponentially-shaped pulses having opposite polarity with respect to adjacent ones of the exponentially-shaped pulses; and
    outputting the exponentially-shaped pulses in bursts of electrical pulses.

3. A device for treating a patient by applying a substance to a patient's skin, comprising:
    a probe configured to apply the substance to the patient's skin;
    an electrical signal pulse generator configured to generate bursts of electrical pulses at a first burst rate;
    a mechanical vibration generator configured to generate a mechanical vibration at a first vibration rate;
    a vibration plate disposed on the probe and coupled to the mechanical vibration generator, the vibration plate configured to provide the mechanical vibration to the patient's skin;

a radio frequency generator configured to generator a radio frequency signal at a fixed radio frequency:

means for applying the radio frequency signal to the patient's skin; and a plurality of electrodes disposed on the probe and coupled to the electrical signal pulse generator, the plurality of electrodes configured to provide the bursts of electrical pulses to the patient's skin, wherein the first burst rate is the same or substantially the same as the first vibration rate.

4. The treatment device according to claim 3, wherein the first vibration rate is within 10% of the first burst rate, or within 10% of a first, second or third harmonic of the first burst rate.

5. The treatment device according to claim 3, wherein each of the bursts of electrical pulses comprises a plurality of pulses in which adjacent ones of said plurality of pulses are of opposite polarity with respect to each other.

* * * * *